United States Patent
Lynch et al.

(10) Patent No.: US 7,214,207 B2
(45) Date of Patent: May 8, 2007

(54) LOW PROFILE, PIVOTAL CONNECTION INFUSION ASSEMBLY

(75) Inventors: George R. Lynch, Coppell, TX (US); Allen E. Brandenburg, Dripping Springs, TX (US); Jeffrey Field, Camarillo, CA (US); Monte Curran, Richardson, TX (US); Andrew Nelson, Dallas, TX (US)

(73) Assignee: Applied Diabetes Research, Inc., Carrollton, TX (US)

( * ) Notice: Subject to any disclaimer, the term of this patent is extended or adjusted under 35 U.S.C. 154(b) by 664 days.

(21) Appl. No.: 10/383,978

(22) Filed: Mar. 7, 2003

(65) Prior Publication Data
US 2003/0216686 A1   Nov. 20, 2003

Related U.S. Application Data

(63) Continuation-in-part of application No. 09/896,149, filed on Jun. 29, 2001, now Pat. No. 6,579,267.

(60) Provisional application No. 60/435,143, filed on Dec. 20, 2002, provisional application No. 60/388,926, filed on Jun. 14, 2002, provisional application No. 60/362,593, filed on Mar. 8, 2002.

(51) Int. Cl.
*A61M 31/00*   (2006.01)

(52) U.S. Cl. .................................. 604/93.01

(58) Field of Classification Search ............. 604/93.01, 604/167.02, 122, 180, 164.01, 164.02, 164.04, 604/164.08, 167.01, 167.06, 890.1, 174, 604/905, 93.04
See application file for complete search history.

(56) References Cited

U.S. PATENT DOCUMENTS

| | | |
|---|---|---|
| 3,547,119 A | 12/1970 | Niles et al. |
| 3,739,778 A | 6/1973 | Monestere, Jr. et al. |
| 3,996,923 A | 12/1976 | Guerra |
| 4,106,491 A | 8/1978 | Guerra |
| 4,126,133 A | 11/1978 | Schwartz |
| 4,258,940 A | 3/1981 | Fudge |
| 4,311,136 A | 1/1982 | Weikl et al. |
| 4,311,137 A | 1/1982 | Gerard |
| 4,418,944 A | 12/1983 | Haines et al. |
| 4,430,081 A | 2/1984 | Timmermans |

(Continued)

FOREIGN PATENT DOCUMENTS

FR    2578746 A1    9/1986

(Continued)

*Primary Examiner*—Cris Rodriguez
*Assistant Examiner*—Laura A. Bouchelle
(74) *Attorney, Agent, or Firm*—Jackson Walker, LLP

(57) ABSTRACT

This invention relates to therapeutic infusion assemblies, more specifically a device for the subcutaneous delivery of a fluid from a remote source. Applicant provides a base assembly which has a fluid channel therein and a cannula extending vertically downward from a flat bottom. A fluid connector member which receives a fluid bearing line from the remote fluid source and the fluid connector member pivotably and removably connects to the base member. The manner of connection is "hinged" allowing the fluid connector to move from a non-use position by rotation downward to a used position. In the use position a fluid channel in the fluid connector will connect with a fluid channel in the base to provide fluid to the cannula and to the patient.

71 Claims, 17 Drawing Sheets

U.S. PATENT DOCUMENTS

| | | |
|---|---|---|
| 4,531,937 A | 7/1985 | Yates |
| 4,645,495 A | 2/1987 | Vaillancourt |
| 4,755,173 A | 7/1988 | Konopka et al. |
| 5,019,054 A | 5/1991 | Clement et al. |
| 5,098,394 A | 3/1992 | Luther |
| 5,176,662 A * | 1/1993 | Bartholomew et al. ..... 604/513 |
| 5,257,980 A | 11/1993 | Van Antwerp et al. |
| 5,281,206 A | 1/1994 | Lopez |
| 5,300,045 A | 4/1994 | Plassche, Jr. |
| 5,330,450 A | 7/1994 | Lopez |
| 5,427,145 A | 6/1995 | Grabenkort |
| 5,545,143 A | 8/1996 | Fischell |
| 5,613,663 A | 3/1997 | Schmidt et al. |
| 5,814,020 A | 9/1998 | Gross |
| 5,848,990 A | 12/1998 | Cirelli et al. |
| 5,851,197 A | 12/1998 | Marano et al. |
| D404,482 S | 1/1999 | Falk et al. |
| 5,858,001 A | 1/1999 | Tsals et al. |
| 5,968,011 A | 10/1999 | Larsen et al. |
| 5,980,506 A | 11/1999 | Mathiasen |
| 6,017,328 A * | 1/2000 | Fischell et al. .............. 604/180 |
| 6,056,718 A * | 5/2000 | Funderburk et al. ..... 604/93.01 |
| 6,093,172 A | 7/2000 | Funderburk et al. |
| 6,095,997 A | 8/2000 | French et al. |
| 6,186,982 B1 * | 2/2001 | Gross et al. ................. 604/132 |
| 6,213,973 B1 | 4/2001 | Eliasen et al. |
| 6,302,866 B1 | 10/2001 | Marggi |
| 6,355,021 B1 | 3/2002 | Nielsen et al. |
| 6,419,699 B1 | 7/2002 | Schuessler |
| 2002/0045867 A1 | 4/2002 | Nielsen et al. |
| 2002/0123724 A1 | 9/2002 | Douglas et al. |

FOREIGN PATENT DOCUMENTS

WO     WO 8702422 A1 *   4/1987

* cited by examiner ( SECTION A-A )

( DETAIL B )

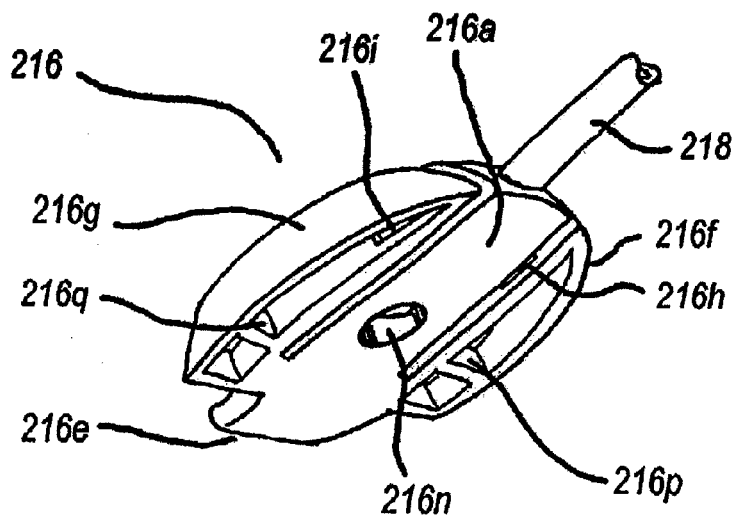
Fig. 15
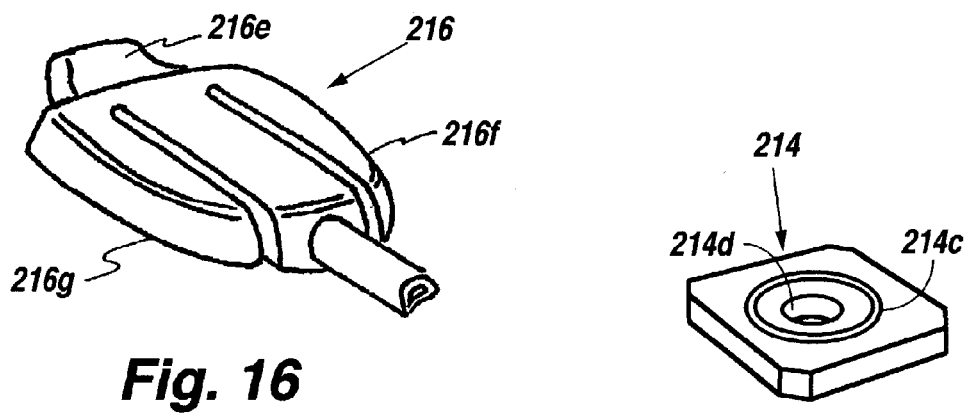
Fig. 16
Fig. 17
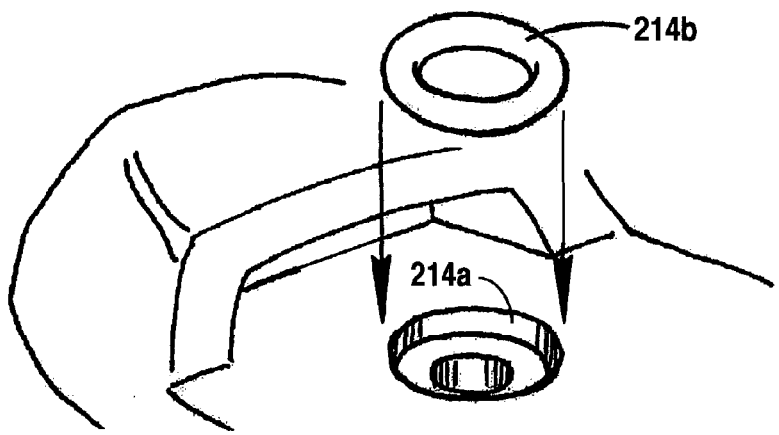
Fig. 18

LOW PROFILE, PIVOTAL CONNECTION INFUSION ASSEMBLY

This application is a continuation-in-part application and claims priority to U.S. patent application Ser. No. 09/896,149, filed Jun. 29, 2001 now U.S. Pat. No. 6,579,267, and U.S. Provisional Patent Applications Ser. Nos. 60/362,593, filed Mar. 8, 2002; 60/388,926, filed Jun. 14, 2002; and 60/435,143, filed Dec. 20, 2002; all of which are incorporated herein for all purposes.

BACKGROUND OF THE INVENTION

This invention relates to therapeutic infusion assemblies and, more specifically, to a device for subcutaneous delivery of a fluid to a patient. The present invention provides an infusion set having a pivoting fluid connector and a base assembly having a base unit and a molded septum. The invention is easy to manufacture and assemble and is simple to use.

Prior art infusion sets provide a number of ways for engaging a fluid connector to a base. The base typically has a vertical cannula depending downward from a flat bottom. The fluid connector typically has a fluid line carrying fluid from a remote reservoir to the base. The fluid connector is typically adapted to being removed from the base of the infusion assembly so that one may have freedom of movement, by disconnecting the fluid connector and leaving only the base attached to the patient.

Many prior art infusion assemblies use septums, piercable with a needle. The septums perform one or more functions. For example, prior art infusion assemblies use a septum with a hollow needle for repeatedly piercing the septum. The piercing needle is normally a part of the fluid connector and adapted for delivery of a fluid from a remote reservoir through the needle to the patient. The base assembly usually includes a cannula which will receive the fluid and introduce it into the patient. The prior art shows that the septums also receive an insertion needle for initially affixing the infusion assembly to the patient.

One of the typical functions of a septum is to releasably seal a chamber, usually within a base assembly, when a needle is urged through it and subsequently removed. A septum may be disk shaped or tabular shaped and defines a wall that seals or separates two cavities. It is typically soft enough to be pierced repeatedly by a needle and reform its shape when the needle is removed. It may or may not include a self sealing slit. Further, the walls of the septum are typically under some compression such that when a needle is removed, resiliency will allow the septum to reform its integrity and maintain the seal between two cavities.

In a preferred embodiment of the present invention, a base assembly includes a septum. The base assembly has a cannula, and the cannula has a lumen axis. A septum in the base assembly aligned with the lumen axis is provided so that the insertion needle may be used to pierce the septum, passing through the cannula and setting the infusion assembly onto the patient. In the septum, vertical and horizontal channels are typically provided. The vertical channel is generally vertical with respect to the flat bottom of the base and the horizontal channel is horizontal with respect to the base. The vertical and horizontal channels are in fluid communication. The junction of the two channels is below that section of the septum intended for receiving the insertion needle.

Also provided is a novel fluid connector for pivotal engagement with the base assembly. The fluid connector has a fluid channel therein. The base assembly and the fluid connector are adapted such that the fluid connector may move from a first (non-operational) position to a second position (operational). The operational position provides fluid engagement with the horizontal channel of the base assembly to the fluid channel in the fluid connector. That is, the base assembly and the fluid connector are designed such that they pivotally engage to move the fluid connector from an operational position wherein the fluid channel therein is in axial alignment and in fluid communication with the horizontal channel of the base assembly (sometimes also referred to as a "use" or "down" position) to a non-operational position wherein the fluid channel of the fluid connector is parallel to the vertical channel of the base assembly and perpendicular to the horizontal channel of the base assembly (sometimes also referred to as the "nonuse" or "up" position).

Another feature of the present invention is a hinged leg having a foot section extending perpendicularly therefrom. The hinged leg may be part of the base assembly. In a first position biased upwardly and adjacent a fluid entry portal in the septum, the foot of the hinged leg blocks the entry portal to prevent material from entry or exit from the portal. In this blocking position, the fluid connector is not engaged with the septum and fluid is not communicating through the base assembly into the patient. When the fluid connector is engaged with the base assembly in operational positions, the hinged leg is urged downwardly and the foot is no longer blocking the entry portal. When the fluid connector is aligned in this arrangement fluid may be delivered through the infusion assembly and into the patient.

SUMMARY OF THE INVENTION

An infusion assembly having, typically, three main parts is disclosed. The first part is a single piece septum having a first channel and a second channel. The first channel is open at a first end thereof and intersects the second channel. The second channel is generally perpendicular to the first channel and open at the bottom end thereof.

A second main part of the infusion assembly is a base unit. The base unit has a flat bottom plate adapted to either lay adjacent the skin of the patient or be attached to a flexible adhesive member which, in turn, will adhesively and removably attach to the skin of the patient. The base unit further includes a soft rubber or plastic cannula which depends generally perpendicularly downwardly from the under surface of the bottom plate for insertion beneath the skin of the patient. The base unit also may include a shoulder and a pair of spaced apart, vertically oriented sidewalls which will function to guide a fluid connector from a first up or elevated position to a second down position. The base unit may also further include a biased or hinged leg member having a proximal end which is pivotally attached to the bottom plate and a distal or removed end having a perpendicularly extending foot which is normally biased upwardly above the bottom plate. The leg member is capable of pivotal movement between an elevated position where the distal end of the leg (the foot) occludes or blocks an entry portal defined by the first channel opening of the septum. The leg member is further capable of movement to a depressed position where the distal end is below or beneath the first channel opening. In the depressed position the leg member may be substantially flush with an upper surface of the bottom plate of the base unit. The base unit further includes means, such as arms, for releasably maintaining the fluid connector in a down position. The base is further dimensioned for receiving and positioning the septum such that the second channel of the septum is aligned with the cannula.

As will be understood further below, the septum and the base unit form the base assembly. While this disclosure discusses the base unit and septum as separate parts, it should be further understood that they may be molded in a unitary fashion or molded separately.

The third major element of the infusion assembly is a fluid connector having a near end, a bottom surface, a vertical wall and a lip at the removed end thereof. The lip is provided for pivotal engagement with a shoulder of a fluid connector engaging member of the base unit. The fluid connector includes walls adapted to engage the spaced apart sidewalls of the base unit such that the fluid connector is capable of pivoting from an up position to a down position. The fluid connector also has a fluid delivery channel therein which will lay adjacent the first channel opening of the septum when the fluid connector is in the down or operational position.

In the second preferred embodiment provision is made for legs, protruding vertically from a base unit acting to hold and push forward for good seating, the base unit against the septum. The second embodiment may feature a single durometer one piece septum that is designed to "pop" into the base unit for easy assembly. The septum typically includes a raised "nose" portion to assist in joining the septum to the fluid connector for a seal type fit between the septum and the fluid connector. Applicants also provide a relatively smooth top surface to the fluid connector.

An alternate preferred embodiment of the present invention provides a base unit formed to provide both vertical and horizontal channels, for engagement with the fluid connector wherein the septum is placed above the vertical channel of the base unit.

A preferred embodiment of the present invention also provides an alternative structure to a septum which has a number of advantages. Instead of utilizing a septum to seal a chamber, the present invention uses paired members. One member is typically on a base assembly having a fluid channel while the other is on a joint pivoting with respect to the base assembly. At least one of the paired members is compressible when the pivoting member is rotated into a position which allows the noncompressible and the compressible members to join. The paired members join to form a fluid sealing joint. A fluid channel in a fluid connector (a fluid connector bearing one of the member pairs) is joined to a fluid channel in the base (the base including the second of the paired members). At least one resilient member, either on the pivoting member or on the base assembly, contacts the other member (in fluid sealing relation) as pivoting action brings the channel in the fluid connector into fluid communication with a cannula mounted on the base assembly. These paired members may take a number of configurations as set forth in more detail below, but typically are incorporated into the novel stationary base/pivoting fluid connector combination to allow for a simple and effective compressive seal between a fluid connector and a cannula bearing base.

BRIEF DESCRIPTION OF THE DRAWINGS

FIG. 2B also illustrates the hinge member urged or depressed downwardly.

FIG. 15 is a bottom perspective view of the fluid connector of the present invention.

FIG. 16 is a top perspective view of the fluid connector.

FIG. 17 illustrates one embodiment of an elastomeric seal of the present invention.

FIG. 18 is an exploded perspective view of a sealing arrangement of the present invention.

DETAILED DESCRIPTION OF THE PREFERRED EMBODIMENT

Figure 1A:
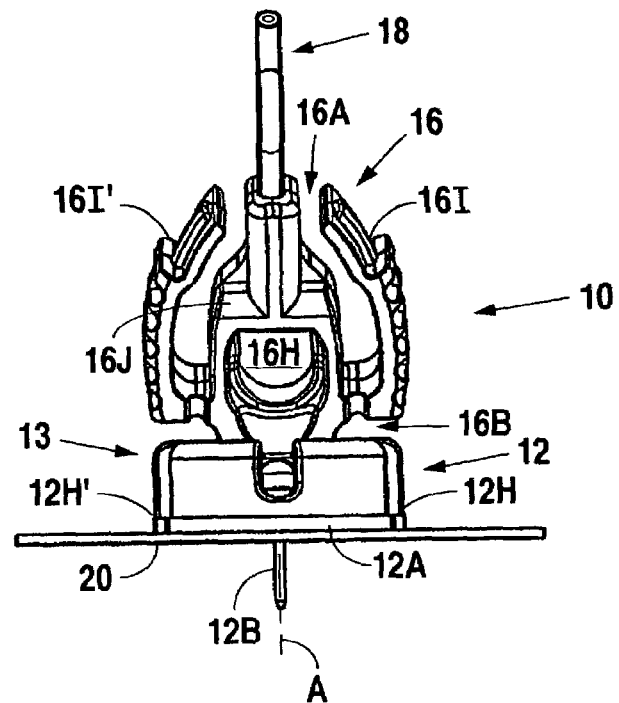
FIG. 1A is a front elevational view of infusion assembly of the present invention showing the base assembly including the septum and the fluid connector engaged therewith. The fluid connector is positioned with respect to the base assembly in an "up," "non-operative," or "nonuse" position.

As illustrated in the attached Figures, infusion system 10 is provided to deliver a fluid, typically carried through a fluid delivery tube 18 into the body of a patient typically through a cannula 12B.

The infusion system or assembly has been reduced to a minimum number of pieces. This simplifies construction, assembly and use of the device. In one embodiment of the invention three fundamental and basic pieces typically are separately manufactured to construct the infusion assembly and include: base unit 12; septum assembly 14; and fluid connector 16. The base and septum form the infusion body assembly 13. In use on the patient, the assembly thus consists of two removably assembled pieces—body assembly 13 (from base 12 and septum assembly 14) and fluid connector assembly 16. In another embodiment discussed below the septum is eliminated by using mating, complementary sealing members.

One function of the base unit 12 in systems having a septum is to provide support for the septum and the fluid connector and to position them with respect to each other so they may pivotally engage one another in a manner set forth below. The base assembly also includes a cannula 12B which is capable of receiving an insertion needle (see FIGS. 3A–3D) for emplacement of the base assembly adjacent the skin with the cannula depending downward through and beneath the skin, for delivery of fluid from a remote reservoir through the fluid connector, septum and the cannula of the base and into the patient.

To accomplish these and other functions, the base unit is seen to include a generally planar, flat bottom surface 12A for resting directly against the skin of a patient or against a double-sided adhesive pad 20 (see FIG. 1A) for removably attaching the assembly indirectly to the skin of a patient.

With reference to FIGS. 1A–2D, it is seen that above the bottom surface of the base 12 are walls 14W defining a septum seat 12I on which a septum assembly 14 may rest as set forth in more detail below. A portion of the base, typically defining a depression therein, includes a cannula seat 12J dimensioned to receive an annular lip 12L of a cannula. A cannula 12B of soft rubber or plastic depends downward perpendicular to the flat bottom surface 12A of the base. The cannula may be sonic welded into the separately molded base prior to assembly of the product.

Figure 1B:
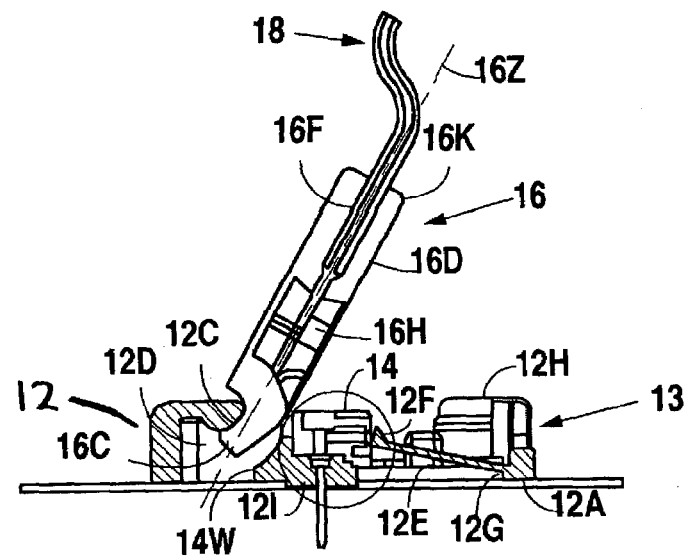
FIG. 1B is a side elevational cutaway view of the infusion assembly of FIG. 1 with fluid connector engaged to the base assembly.

As set forth in FIG. 1B, the base 12 also includes a shoulder 12C which serves as a first hinge section. The shoulder comprises a horizontal arm designed for engagement of the fluid connector as seen in more detail below. Adjacent the shoulder are a pair of spaced apart vertical opposed sidewalls 12D (one of the pair shown in FIG. 1B). These sidewalls 12D, also serving as a portion of the first hinge section, are designed to engage corresponding sidewalls of the fluid connector when lip 16C is engaged with the shoulder 12C to hingedly and pivotally guide the fluid connector on to the septum assembly, the septum assembly having been mounted to the base in the assembly process.

Figure 1C:
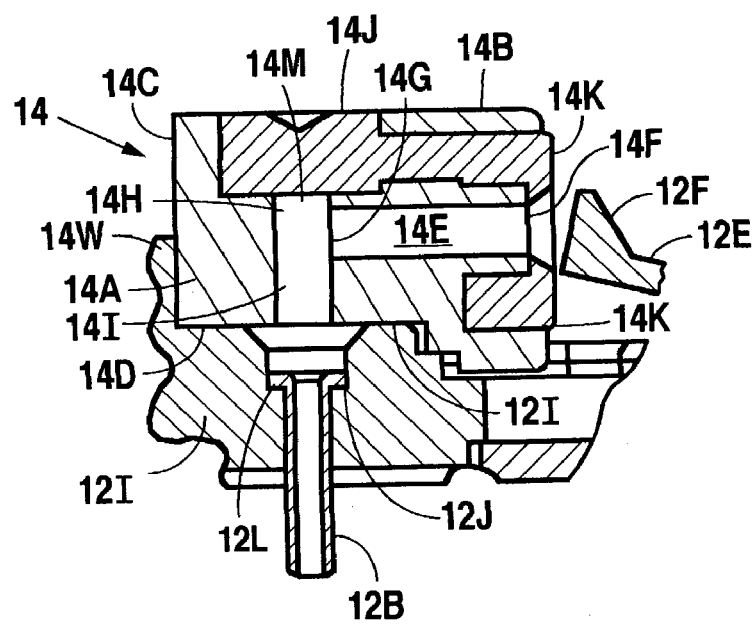
FIG. 1C is a partial cutaway elevational view of base unit and septum of the present invention illustrating the septum joined to the base unit and the septum body having a vertical channel axially aligned with the vertical axis of the base unit cannula. A horizontal channel perpendicular to the vertical channel is also illustrated.
Figure 1D:
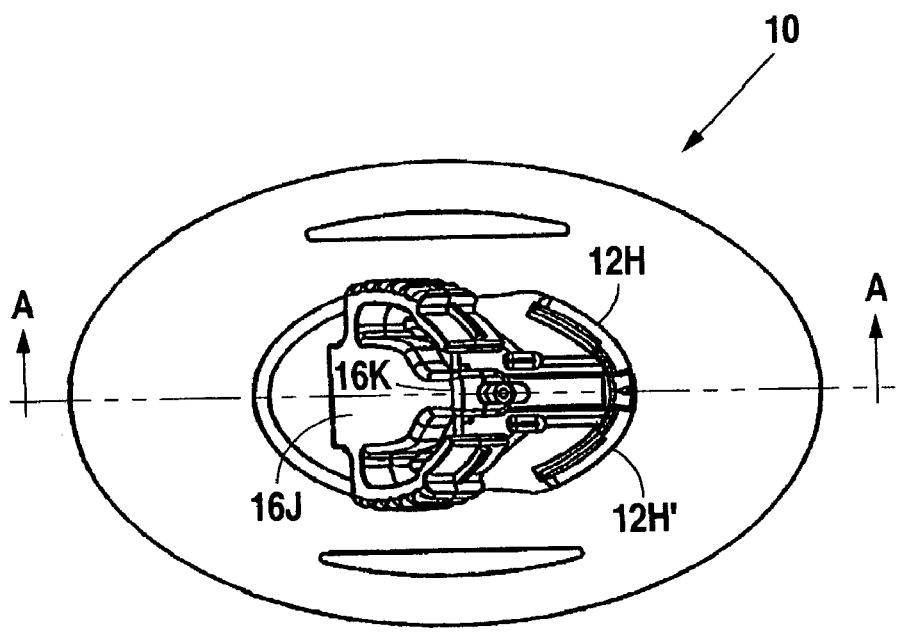
FIG. 1D is a top elevational view of the infusion assembly of the present invention illustrated in FIG. 1A.

The base may include a protector assembly having an orifice blocking leg 12E, the leg being an extended member having a foot portion 12F at the removed end thereof. The foot portion 12F extends generally perpendicularly from the longitudinal axis of the leg. The leg is attached at a near end 12G by an integral (living) hinge, to the base 12. In the manufacture of the base blocking, leg 12E is biased so that foot portion 12F is elevated above the bottom surface of the base as illustrated in FIGS. 1B and 1C, for example. The base is manufactured from a material, such as plastic, that has some resiliency and is molded with the leg in the "up," "blocking," or occluding position as illustrated in FIGS. 1B and 1C. The leg is attached at its near end 12G in a manner such that it pivots downwardly easily about the near end from its normally upwardly biased position. Thus, near end 12G acts as a "living hinge" incorporated into the leg and base. Base 12 may also have a pair of fluid connector arm engaging members 12H and 12H' (see FIG. 1D), to resiliently engage arms 16I and 16I' of the fluid connector to hold the fluid connector in a down or delivery position.

As seen in FIG. 1C, a septum assembly 14 has a septum body 14A, having a hardness of a first durometer reading. The septum assembly typically includes a top surface 14B, sidewalls 14C and a bottom surface 14D. In a preferred embodiment the septum assembly 14 includes a fluid flow channel therein. A horizontal, first channel leg 14E has an open first end 14F and an open second end 14G. The second end 14G opens to a vertically aligned second channel leg 14H. The second channel leg 14H has a first end 14I leading to the cannula and a second end 14M leading to a second end 14G of the first channel leg 14F. As noted with respect to FIG. 1C, septum assembly 14 may be glued or otherwise secured to septum seat 12I. The septum assembly may be a single durometer sufficient for the insertion needle to penetrate or it may have two areas of differing durometers at least one part of the top surface thereof being of a durometer penetratable by an insertion needle.

For example, a soft septum member 14J may be incorporated into the septum assembly through the use of a "two shot" molding method and likewise, there may be a sidewall portion 14K which is of a softer durometer than the remainder of the septum body. In such an embodiment a portion of the septum member is positioned above the first channel 14E. It is to be pointed out, however, that the septum is typically shot as a single unit—not two units separately manufactured and then glued or welded together, as is known in the prior art. It is typically a single piece septum assembly which may have areas of softer durometer, for example, so as to provide easier receipt of the insertion needle in puncturing the top surface 14B. Sidewall port 14K may be, preferably, ring shaped encircling as it is the port opening provided in septum body 14A by open first end 14F of first channel 14E.

First channel leg 14E and second channel leg 14H are generally perpendicular to one another, the first channel leg is typically horizontal and the second channel leg typically vertical. When the fluid connector is in a down position, it is able to deliver fluid to the septum assembly fluid channel via first end 14F of first channel leg 14E, through the septum assembly 14 until the fluid reaches the second end 14G of first channel leg. The fluid is then delivered to the second channel leg 14H, where it flows downward under the impetus of gravity (or a feed pump, not shown) into the cannula for delivery into the body of the patient.

Figure 2A:
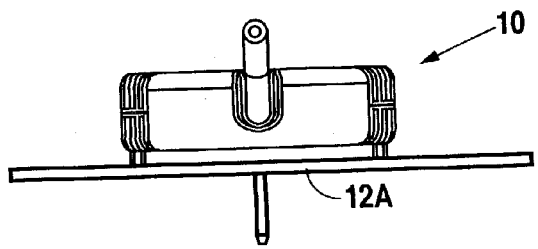
FIG. 2A is a front elevational view of the infusion assembly of the present invention with the fluid connector in a "down", "operational," or "use" position.
Figure 2B:
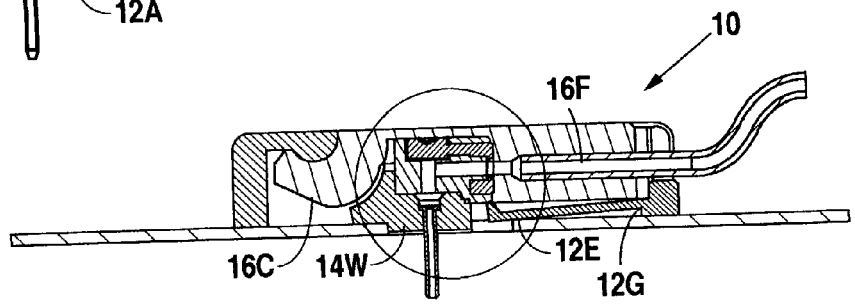
FIG. 2B is a side elevational cutaway view of FIG. 2A illustrating the manner in which the fluid channel of the fluid connector axially aligns with the horizontal channel of the septum/base assembly when in a down or use position.
Figure 2C:
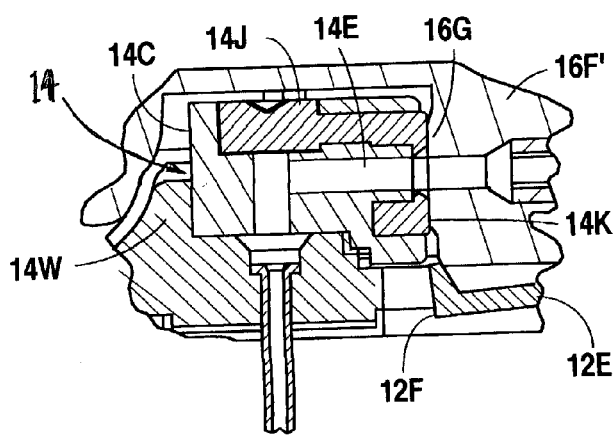
FIG. 2C is a partial cutaway view of the septum body showing vertical and horizontal fluid channels therein. The fluid connector is in the down or use position (as illustrated in FIGS. 2A and 2B) further illustrating the manner in which a base wall of the fluid connector may snugly engage a vertical wall of the septum so as to align the horizontal channel of the septum with the fluid channel of the fluid connector and provide a fluid flow path through the fluid channel of the fluid connector into the cannula of the base assembly.

A fluid connector 16 is provided for engagement with the base 12 of the body assembly 13 in a rotatable fashion and is pivotable on the base for alignment with the septum assembly to deliver fluid from the fluid delivery tube 18 to the fluid flow channel of the septum assembly when the fluid connector has been rotated to a down or operational delivery position (see FIGS. 2B and 2C).

Figure 2E:
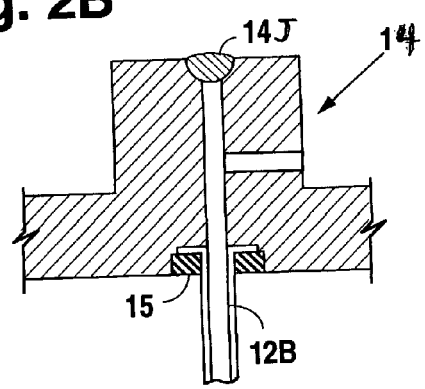
FIG. 2E is an alternate preferred embodiment of the present invention, wherein the base unit includes the vertical and horizontal channels and a piercable septum is located atop the vertical channel of the base assembly.
Figure 2D:
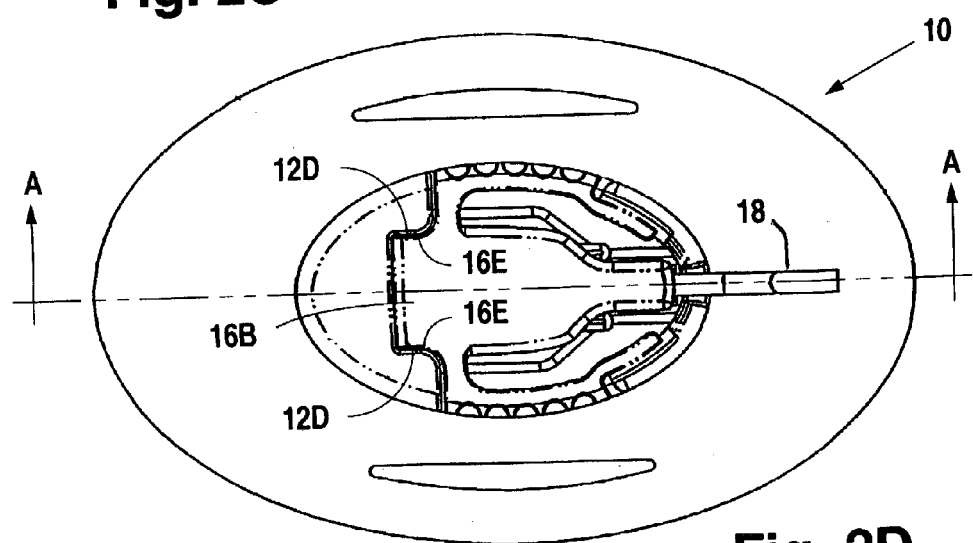
FIG. 2D is a top elevational view of the fluid connector engaged with the base assembly and the fluid connector in the down or use position.
Figure 3A:
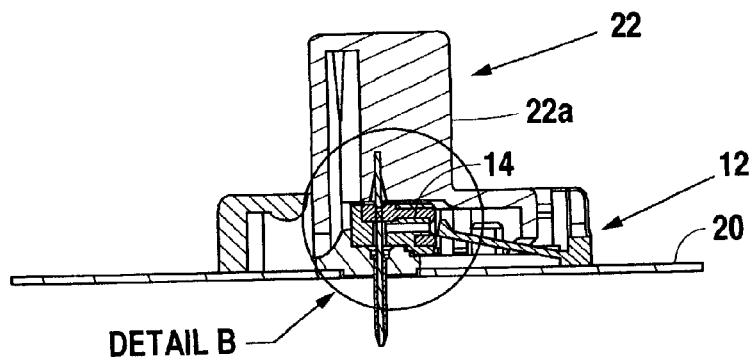
FIG. 3A is a side elevational cutaway view of the base and the septum of the present invention without the fluid connector but with an insertion needle assembly in place.
Figure 3B:
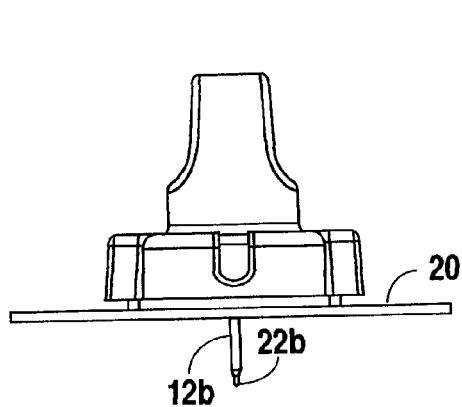
FIG. 3B is a front elevation view of FIG. 3A.
Figure 3C:
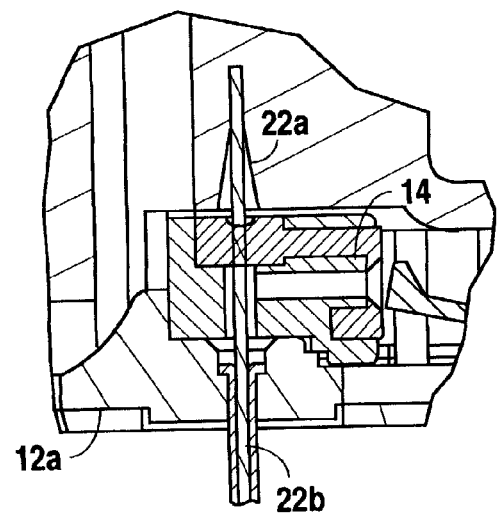
FIG. 3C is a partial front sectional view of the insertion needle in place penetrating the septum and aligned with and partially within the cannula to allow for placing the base assembly of the infusion assembly on a patient.
Figure 3D:
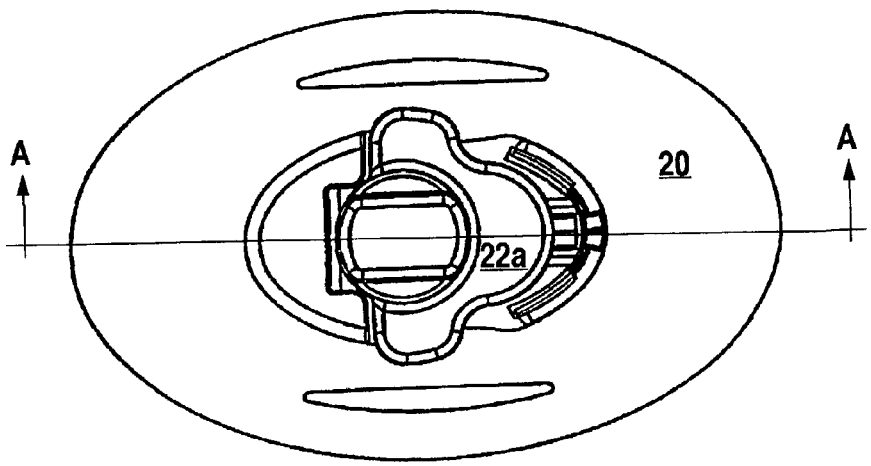
FIG. 3D is a top elevation view of the representations set forth in FIGS. 3A and 3B.

To accomplish this and other objects, fluid connector 16 is seen to have a near end 16A, a body 16J, and a nose 16K projecting from the body (see FIGS. 1A, 1B, 1D and 2D). Opposite near end (16A) is a removed end (16B). The fluid connector has a longitudinal axis 16Z. Removed end 16B includes a lip 16C which serves as a portion of a second hinge section. The lip is designed for pivotal engagement with shoulder 12C of base 12. The fluid connector includes a pair of spaced apart sidewalls (16E)(see FIG. 2D) which also serve as a part of the second hinge section and engage flush adjacent the spaced apart sidewalls (12D)(see FIGS. 1 and 1B) of the base. Thus, a mechanism is provided for the fluid connector to easily and removably engage the base at the shoulder while providing paired adjacent sidewalls to guide the fluid connector from an up or non-delivery position (FIGS. 1 through 1D) to a delivery or down position (FIGS. 2 through 2D).

Fluid connector 16 also includes a bottom surface 16D. The bottom surface includes at least a portion thereof dimensioned to interfere with foot 12F of leg 12E as the fluid connector moves towards the down position to urge the foot away from first end 14F of fluid flow channel 14E. FIGS. 1C, 2C, 1A and 2A illustrate the manner in which the fluid connector in an up position does not interfere with the position of the foot adjacent the first end of the first channel. In this "up" position the foot blocks the channel and prevents the accumulation of harmful material at the first channel. When the fluid connector is in a down position, it is seen that a portion of the bottom surface 16D has interfered with the foot of the leg to urge it to a down position positioning the fluid delivery tube of the fluid connector adjacent the first channel to allow the passage of fluid therethrough.

The bottom surface of the fluid connector may include recessed area 16H (see FIG. 1A) that is contoured to snugly enclose the sidewalls and the top surface of the septum assembly when the fluid connector is in a down position. The snug fluid sealing relationship between raised walls 16G of the fluid connector and the septum assembly may be appreciated, for example, with reference to FIG. 2C. Further, raised walls 16G are seen to define a slightly convex surface which may encircle open end 16F' of fluid delivery channel 16F. This is best seen in FIG. 2C. Raising the walls in this fashion, along with providing septum assembly 14 with a raised ring shaped sidewall port 14K provides a fluid tight seating arrangement between the fluid connector and the septum such that fluid flowing from open end 16F' into first channel leg 14E will not leak out. Some resiliency in sidewall port 14K is, therefore, desirable. Note that the bottom surface of the fluid connector is dimensioned to allow interference with foot portion 12F of leg 12E while the fluid connector is urged into the closed position.

FIG. 2E illustrates an alternative base 12 and septum assembly 14 arrangement in which the base 12 has molded therein a vertical and horizontal channel. A septum member 14J, made of a durometer soft enough for an insertion needled to be emplaced, sits atop the vertical channel leg, which is aligned with the lumen of the cannula. The base and the fluid connector still pivotally engage. The fluid connector moves from a delivery position where the fluid channel and the fluid connector is aligned with the horizontal channel of the base to a non-delivery position wherein the two channels are out of alignment. Other features noted in this alternative embodiment of FIG. 2E is the absence of a living hinge (though one may be provided). Further, it can be seen that a cannula retainer plate 15 may be used to improve the sealing of the cannula against the base.

FIGS. 3A through 3D illustrate an infusion set without the fluid connector but with the insertion needle assembly 22 engaged therewith. More specifically, insertion needle assembly 22 includes a handle 22A and a needle 22B. The needle is inserted through a top portion of the septum vertically downward through the second channel and the cannula until the removed end of the needle sticks out just past the removed end of the cannula (see FIG. 3B). It is in this configuration that one gently inserts the needle/cannula into a patient so that the cannula will depend downward underneath the skin such that the base or the adhesive member 20 will lay adjacent the skin The handle may then be removed and discarded. The fluid connector 16 may be attached in an up position for pivoting downward and commencing delivery of fluid to the patient.

FIGS. 4A through 4F illustrate a base 112 of yet another embodiment of the present invention, illustrating an alternate manner of pivotally holding or engaging the fluid connector to the body.

Figure 6A:
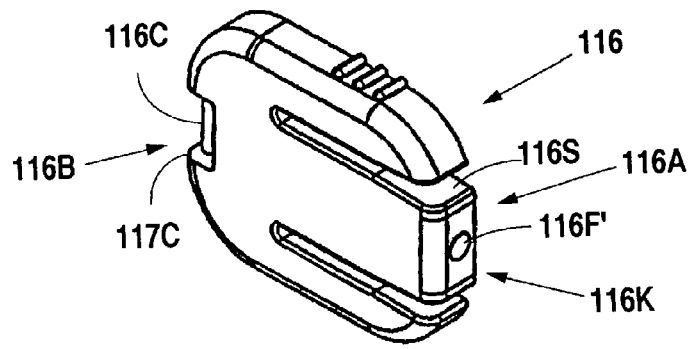
FIG. 6A is a perspective view showing an embodiment of a fluid connector of the present invention for use with the base illustrated in FIGS. 4A–4F above.
Figure 6D:
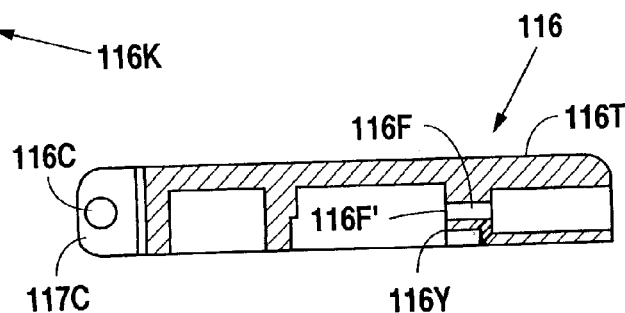
FIG. 6D is a cross sectional view of the fluid connector of FIG. 6A.
Figure 6B:
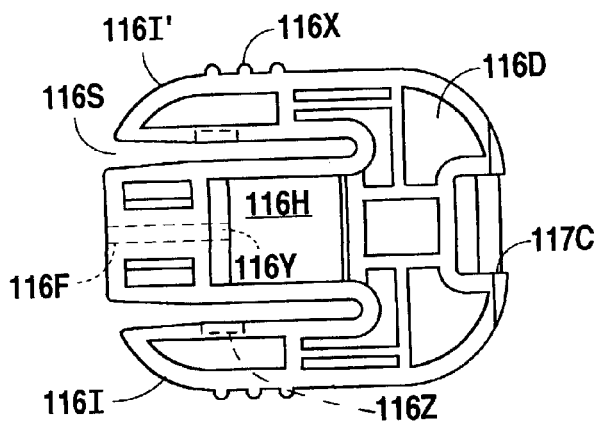
FIG. 6B is a bottom elevational view of the fluid connector of FIG. 6A.
Figure 6E:
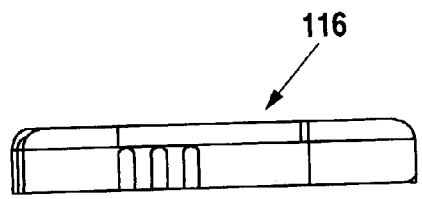
FIG. 6E is a side elevational view of the fluid connector of FIG. 6A.

As seen in FIGS. 4A–4F, arm engaging members 112H and 112H' project vertically from and integral with base 112 which will resiliently engage arms 116I and 116I'(see FIG. 6B) of the fluid connector in a manner that will enclose the arm engaging members when the fluid connector is in a down or use position.

Figure 4A:
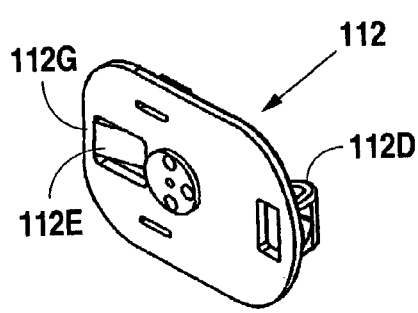
FIG. 4A is a perspective view showing the under surface of a base of an alternate preferred embodiment of the present invention, the base illustrated in FIGS. 4A–4F for use with the fluid connector illustrated in FIGS. 6A–6F.
Figure 4B:
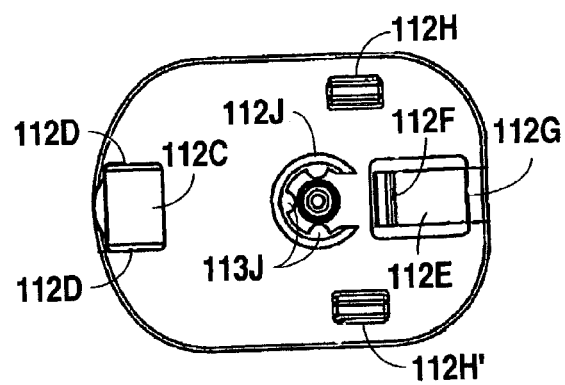
FIG. 4B is a top elevational view of a base of an alternate preferred embodiment of the present invention.
Figure 4C:
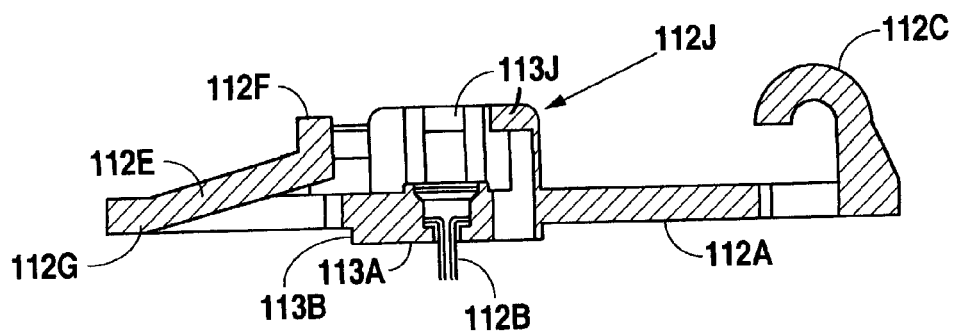
FIG. 4C is a cutaway side elevational view of a base of an alternate preferred embodiment of the present invention of the section illustrated in FIG. 4D.
Figure 4D:
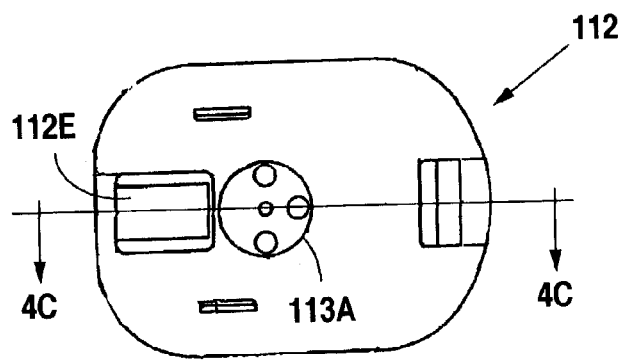
FIG. 4D is a bottom elevational view of a base of an alternate preferred embodiment of the present invention.
Figure 4E:
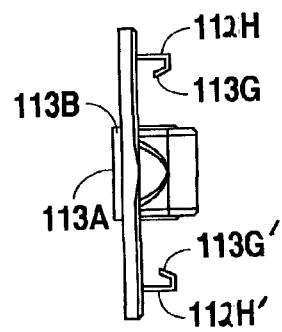
FIG. 4E is a rear elevational view of a base of an alternate preferred embodiment of the present invention.
Figure 4F:
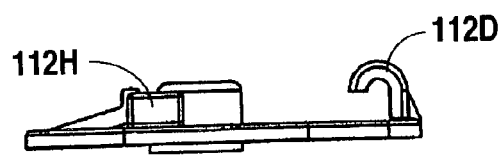
FIG. 4F is a side elevational view of a base of an alternate preferred embodiment of the present invention.
Figure 5A:
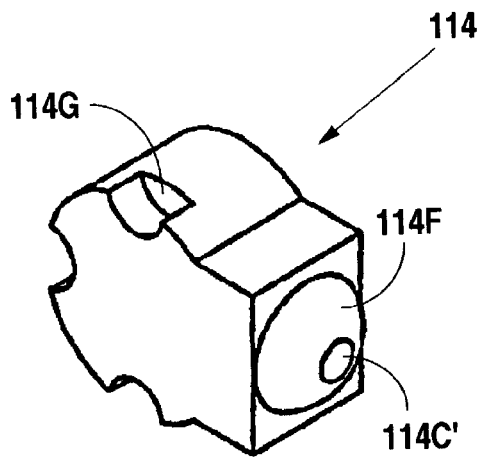
FIG. 5A is a perspective view of a septum for use with the present invention.
Figure 5B:
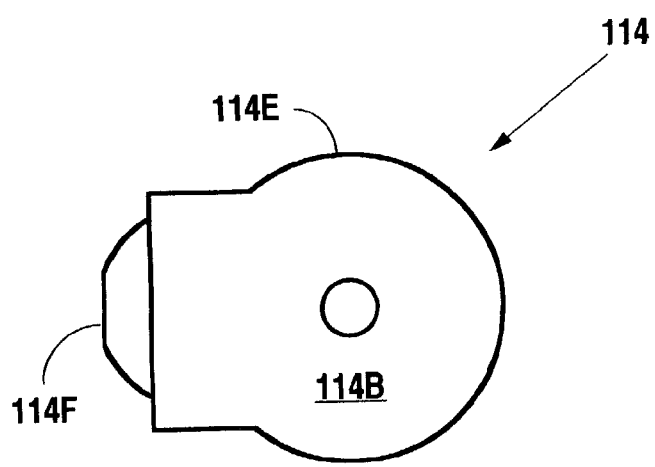
FIG. 5B is a bottom elevational view of the septum of FIG. 5A.

It may also be appreciated with reference to these illustrations that the novel septum 114 shows a raised nose 144F (FIGS. 5A and 5B). It may be appreciated that the raised nose will help insure a good fit to the fluid connector when the fluid connection is in a down position to help insure the integrity of the septum/fluid connection interface. Septum 114 is also seen to be a single piece, single shot device. As seen in FIGS. 4B and 4C, base 112 may include resilient septum engaging bosses or tabs 113J (here three) for resiliently holding and positioning the septum engaged with the base, by engagement with similarly dimensioned notches 114G (see FIG. 5A) in the septum.

Figure 6C:
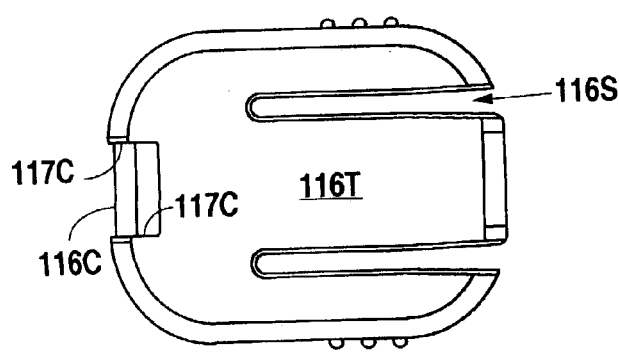
FIG. 6C is a top elevational view of the fluid connector of FIG. 6A.
Figure 6F:
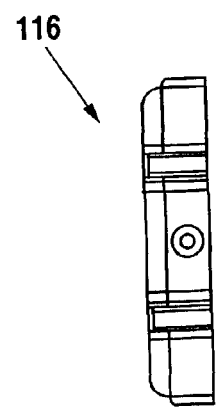
FIG. 6F is a front elevational view of the fluid connection.

FIGS. 4A through 4F illustrate details of the alternative base 112. FIG. 4C shows that the base features a downwarding depending cannula 112B. The cannula depends from a flat bottom surface 112A. Optionally, a stepped portion 113A of the bottom may include a needle guard lip 113B. Septum housing 112J is designed to receive septum 114 (see FIG. 5A) therein and may do so via the engagement of tabs 113J with notches 114G in the resilient septum. Lip portion 112C includes hook sidewalls 112D. Hook portion and hook sidewalls 112D are designed to engage cross-arm 116C of fluid connector 116 (see FIG. 6C). Hook sidewalls 112D will engage sidewalls 117C adjacent cross-arm 116C so as to maintain a uniform guided motion between the open and the closed position of the fluid connector. Thus, hook sidewalls 112D and sidewalls 117C adjacent cross-arm 116C and hook portion 112C engaging cross-arm 116C will function, when engaged, to secure the fluid connector to the base when the fluid connector is in up position and to guide the fluid connector between the up or open position in a closed or down position. The fluid connector will be engaged when in a down position by engagement between the arm engaging members of the base and the arms of the fluid connector as well as engagement at the hook and sidewalls. Engagement of recessed area 116H of fluid connector 116 (see FIG. 6B) with the septum and the septum seat will occur when the fluid connector is in the down position. Leg 112E is seen to have a living hinge and a foot 112F and to function, pivoting with engagement with the fluid connector, in a manner set forth with earlier embodiments.

Arm engaging members 112H and 112H' of base 112 are seen to include lip portion 113H and 113H' such that when the fluid connector is urged to a down position the lip portion may engage corresponding notches 116Z (see FIG. 6B), in the inside sidewalls of the arms 116I and 116I' of the fluid connector to hold the fluid connector in a down position. The sidewalls of the arm engaging members may be canted so that they may engaged in an interfering manner with walls of the fluid connector to urge the fluid connector as it is pushed to a down position towards and against the septum for a good seal.

Figure 5C:
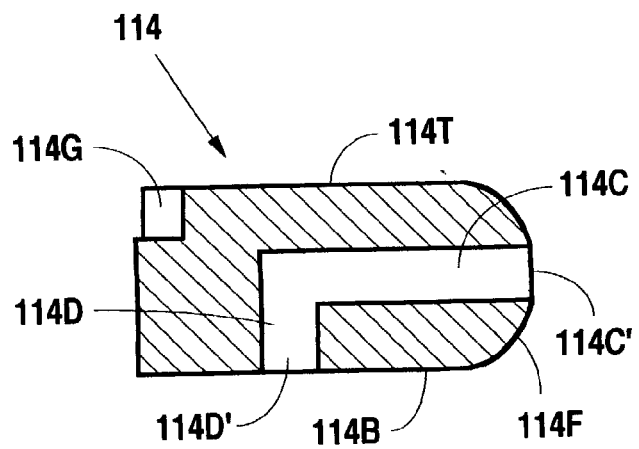
FIG. 5C is a cross sectional view of the septum of FIG. 5A.

FIGS. 5A through 5C illustrate a resilient septum 114 of the infusion system. The septum includes notches 114G which will engage the tabs 113J of the septum seat of the base when the septum 112 is pressed into the seat. Typically, septum 114 also includes a flat top surface 114T for flush engagement with the fluid connector when the fluid connector is in a down position. Bottom surface 114B typically lays flush against the base. In FIG. 5C it is seen that there is a first channel leg 114C with an open end 114C' that is typically parallel to the base and joins a second channel leg 114D with open end 114D', which open end is typically located over the top end of the cannula 112B when the septum is in place on the base.

FIGS. 6A through 6F illustrate a cooperating fluid connector 116 for use with base 112. A smooth top 116T and a pair of resilient arms 116I and 116I' extending forward from the rear portion of the fluid connector are shown. Notches 116Z are on the inner faces of arms 116I and 116I' The arms define slots 116S between the two outboard arms and the centrally located nose 116K. There is some flexibility in the arms allowing them to be squeezed inward for release of the fluid connector from a down position in which the arms are engaged with the arm engaging members of the base. Ribs 116X on the outer surface of the arms provide for finger engagement with the fluid connector arms for ease of moving the fluid connector between a raised and lowered position and for urging the arms inward for release of the fluid connector from the down position.

Fluid connector 116 has a near end 116A and a removed end 116B. Sidewalls 117C are located at removed end 116B. Cross-arm 116C which is designed to removably and snuggly engage lip portion 112C of the base. The hook portion sidewalls snuggly and slidably engage sidewalls 117C of the fluid connector as the fluid connector is moved between a raised and lowered position. On the underside of the fluid connector there is seen a recessed area 116H dimensioned for receipt of the septum and the septum seat. When the fluid connector moves to a down position there is a wall 116Y (see FIG. 6B) that is located so that it interferes with, by contact, the foot portion 112E of leg portion 112F of leg 112E to urge it away from its up or raised position adjacent the nose of the septum to a down position away from the nose of the septum. In the down position open end 116F' of fluid delivery channel 116F snuggly sits adjacent open end 114C' of the septum so fluid may flow through the septum and through the cannula into the patient.

Figure 7:
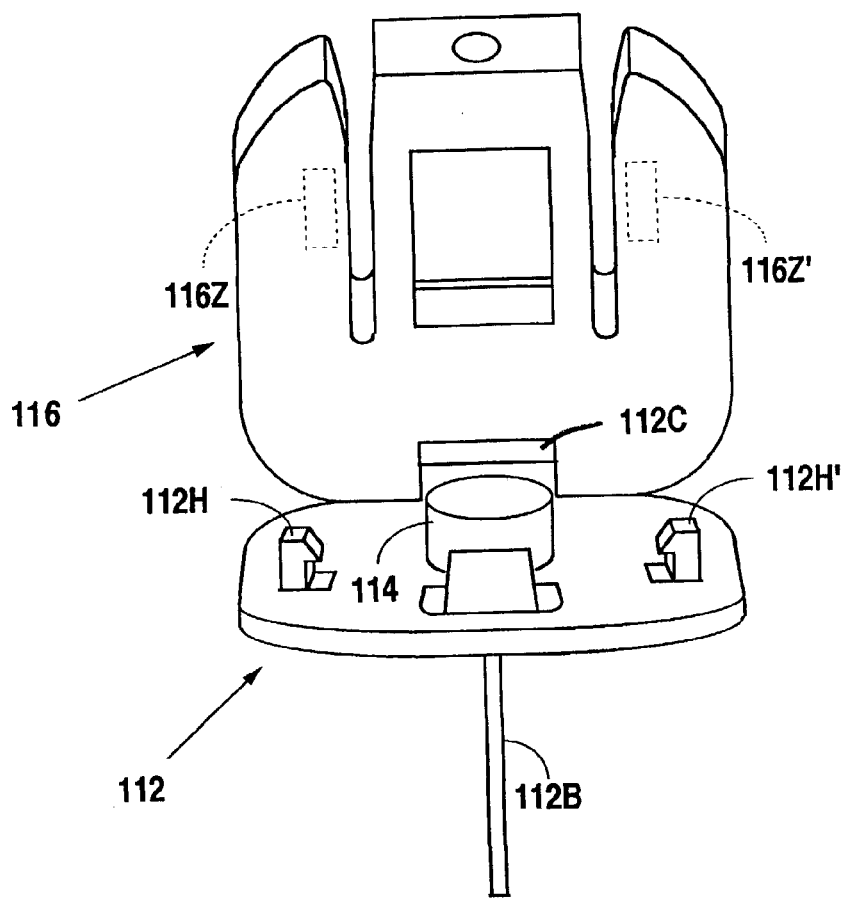
FIG. 7 is a perspective illustration of an alternate preferred embodiment of the infusion assembly of the present invention as illustrated in FIGS. 4A–4F and 6A–6E with the fluid connector in a "non-delivery" or "up" position.

FIG. 7 illustrates the manner in which base 112 as illustrated in FIGS. 4A–4F engages fluid connector 116. The manner of engagement provides hinged movement between the base and the fluid connector. The illustration in FIG. 7 shows hook portion 112C in the base and the manner in which it engages with the fluid connector. The manner of connection is "hinged" allowing the fluid connector to move from a non-use position by rotation downward to a use position. In the use position a fluid channel in the fluid connector will connect with a fluid channel in the base to provide fluid to the cannula and to the patient.

Figures 8A, 8B:
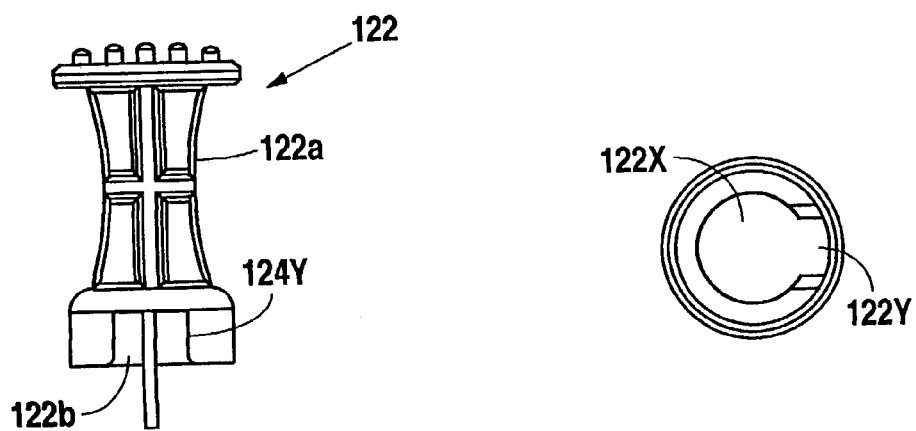
FIG. 8A illustrates an insertion needle assembly for use with a base with the present invention.
FIG. 8B is a bottom plan view of the needle assembly of FIG. 7A.

FIGS. 8A–8B illustrate the needle hub assembly 122. The assembly has a handle 112A and a needle 112B projecting perpendicularly therefrom. The fluid connector is apart from the body of the base when the needle hub assembly engages septum, base and cannula. After the unit is in place upon the user the needle hub assembly may be withdrawn and discarded, and the fluid connector, with the fluid connector line attached, may be engaged to the back and moved from an up position to a lower or use position for providing fluid to the patient from a remote reservoir (not shown). The removed end of the needle assembly includes the hollow portion 112X with the window 112Y cut out therefrom, the hollow portion and window shaped to fit around septum housing 112J of base when the septum is engaged therewith. Interference between the sidewalls of the hollow portion and the window with the septum and the sidewalls of the septum housing may provide a guide to center the needle so that it is properly aligned with the cannula.

Figure 9:
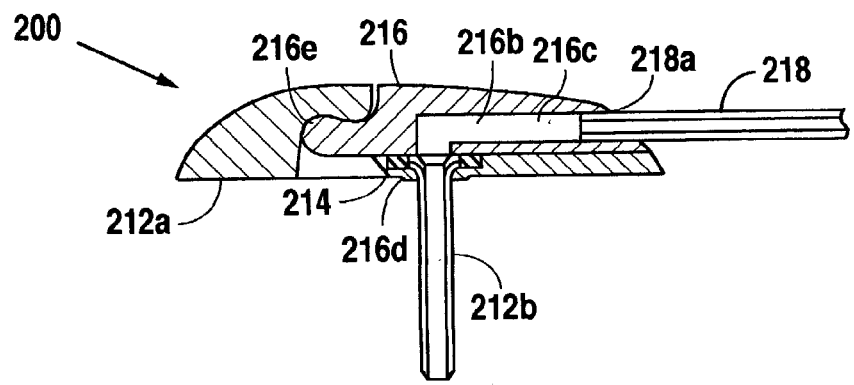
FIG. 9 illustrates a side elevational cross sectional view of a septumless infusion assembly of the present invention.
Figure 10:
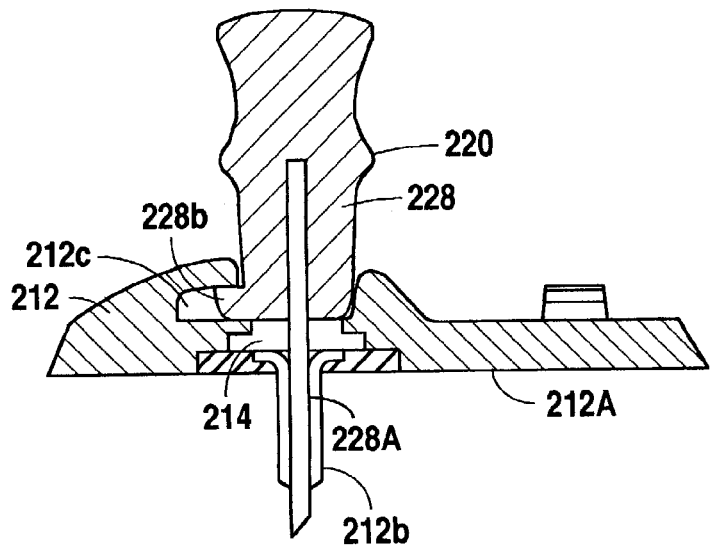
FIG. 10 shows a side elevational cross sectional view of the septumless base with an insertion needle extending through the cannula.

One preferred embodiment of the present invention for a "septumless" infusion system is illustrated in FIGS. 9 through 36. FIGS. 9 and 10 illustrate an alternate preferred embodiment of an infusion assembly 200, the infusion assembly having a base 212, a first sealing member 214, a fluid connector 216 and a fluid delivery tube 218. An insertion needle assembly 220 (see FIG. 10) may be provided for implacement of the infusion assembly on to a patient.

FIG. 10 shows insertion needle assembly 220, the insertion needle assembly including a handle 228 having a needle 228A projecting thereto. A foot 228B may help locate the needle assembly by engagement with cutout portion 212C of the base.

Infusion assembly 200 is seen to be "septumless." It is seen to include a pivoting fluid connector 216 for engagement with a base 212, the fluid connector being rotatable between a use (delivery) and a non-use (non-delivery) position. The base 212 has a flat bottom portion 212A. A soft and flexible cannula 212B is provided and defines a lumen therein. Cannula 212B extends vertically downward from the flat bottom portion of the base.

The base may include walls defining a cutout portion 212C which serves as a hinge section. The cutout is shaped for receipt of a hinge section of the fluid connector as set forth in more detail below. The cutout includes vertical paired sidewalls 212D which will engage and guide the fluid connector (when hingedly engaged with the base) from a non-delivery (or "up") position to a delivery position (or "down" position) as set forth below. The base may include vertically projecting alignment bosses 212E for engagement with the fluid connector to assist in guiding the fluid connector to a down or delivery position. The base may also include vertically upstanding legs 212F and 212G (FIG. 21) for releasable engagement with the arms of the fluid connector to hold the fluid connector in a down or use position. In an alternate preferred embodiment of infusion assembly 212, a slide 213 may be used (see FIGS. 21 through 28), the slide for protectively covering a fluid channel 214D when the fluid connector is either removed from the base or out of its "down" or delivery position as set forth in more detail below.

Figure 11:
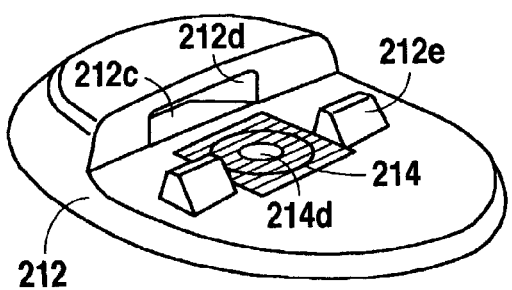
FIG. 11 is a perspective view of the base assembly with a septumless seal.
Figure 12:
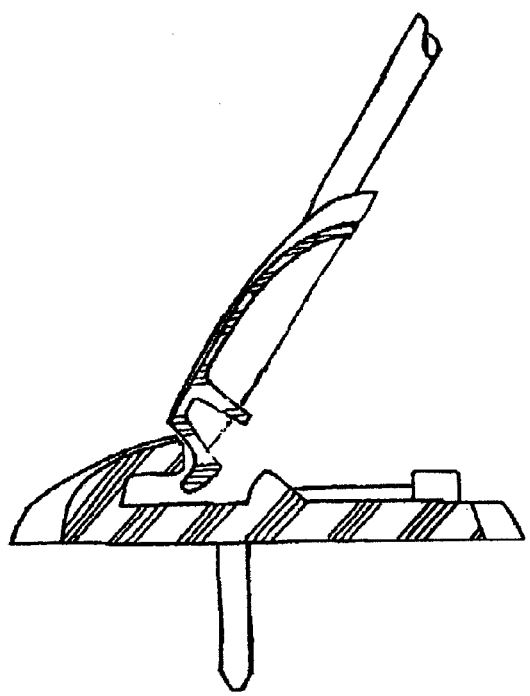
FIG. 12 Is a side elevational, cross sectional view of an infusion assembly in the open, up, or non-operational position.
Figure 13:
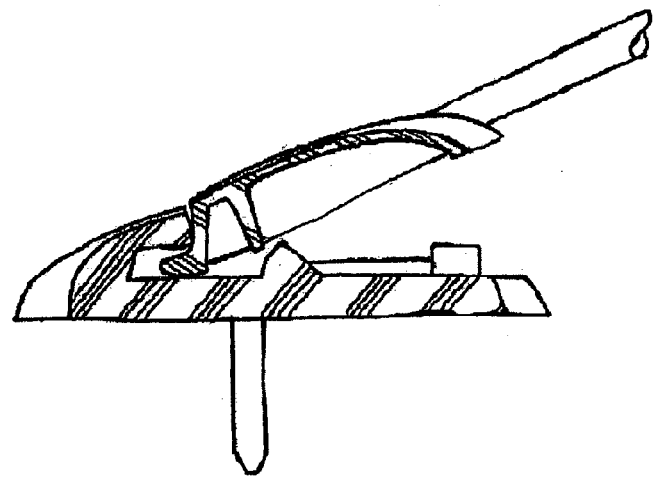
FIG. 13 illustrates the assembly of FIG. 12 in a partial lowered position.
Figure 14:
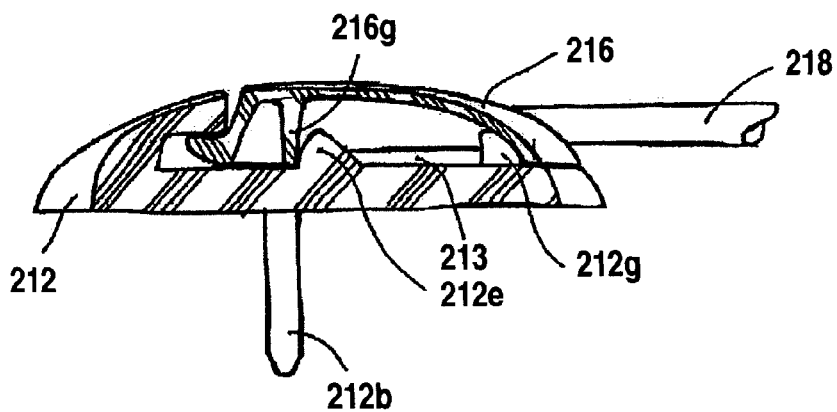
FIG. 14 shows the assembly of FIG. 12 in the closed, down or operational position.

Turning to FIG. 18, the figures also illustrate a first sealing member 214 which typically includes a body portion 214A and may include a resilient "O" ring 214B. The first sealing member is typically at least partially resilient and may include a resilient raised bead 214C (see FIG. 17). In any case, first sealing member 214 typically defines a fluid channel 214D therein and is dimensioned for receipt into base 212 as seen in FIGS. 9 and 11. Thus, first sealing member may be integral with base 212. It can be seen that fluid connector 216 includes a bottom wall 216A and has a fluid channel 216B therethrough (see FIG. 9). Fluid channel 216B may include a first leg 216C and a second leg 216D. Where fluid channel 216B meets bottom wall 216A, a port 216N is defined which port will join, when the fluid connector is in a delivery position, the fluid channel 214D of a first sealing member. The fluid connector typically includes an arm or lip 216E projecting therefrom shaped to engage cutout 212C and sidewalls 212D of base 212 in releasable fashion so that when the lip nests or seats snugly within the cutout, the fluid connector may be rotated from an up position to a down position while being guided onto bosses 212E (which bosses assist with the guidance and alignment of the base with the fluid connector) (see FIGS. 12–14), if used, and such that legs 216F and 216G having leg cutouts 216H and 216I will resiliently and releasably engage legs 212F and 212G to releasably lock the fluid connector to a down position. In approaching the full down position it will be noted that either "O" ring 214B or raised bead 214C will engage the bottom wall 216A of the fluid connector in the area of port 216N in a resilient manner so as to join in fluid sealing relation the port of the fluid connector to a port in fluid communication with the lumen of cannula 212B so that fluid may be delivered through the fluid connector into the body and into the cannula without leaking.

Figure 21:
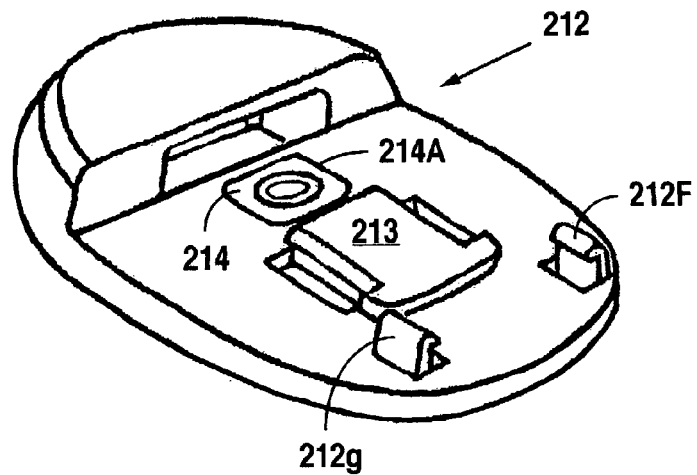
FIG. 21 is a perspective view of a slide assembly of the present invention in the open position.
Figure 22:
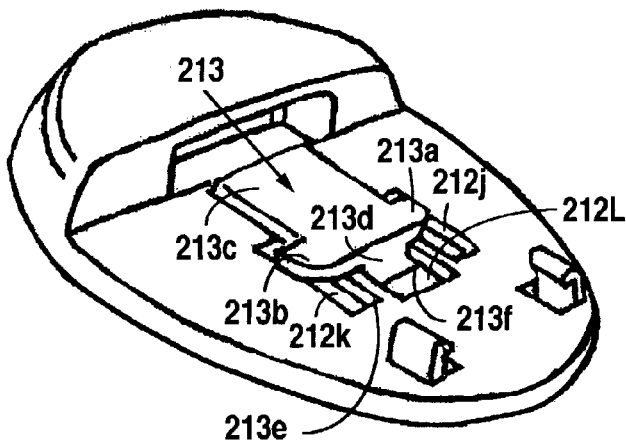
FIG. 22 illustrates the movement of the slide assembly of FIG. 21 to the closed or protected position.
Figure 23:
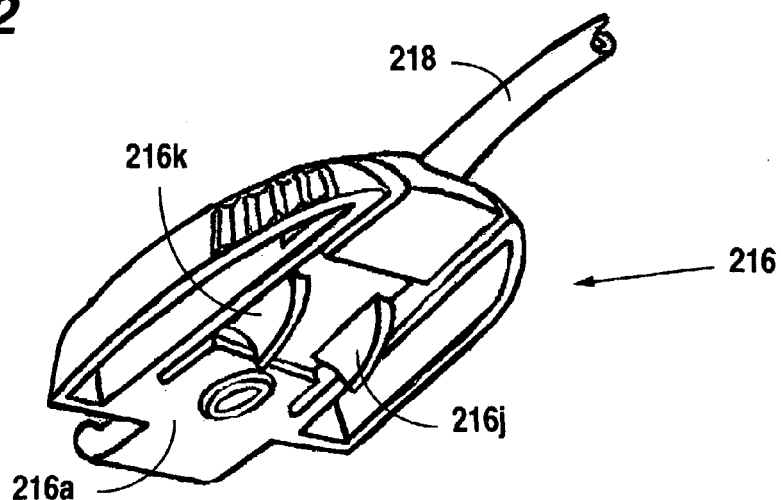
FIG. 23 shows a bottom perspective view of the fluid connector of the present invention with the slide opening cams.
Figure 24:
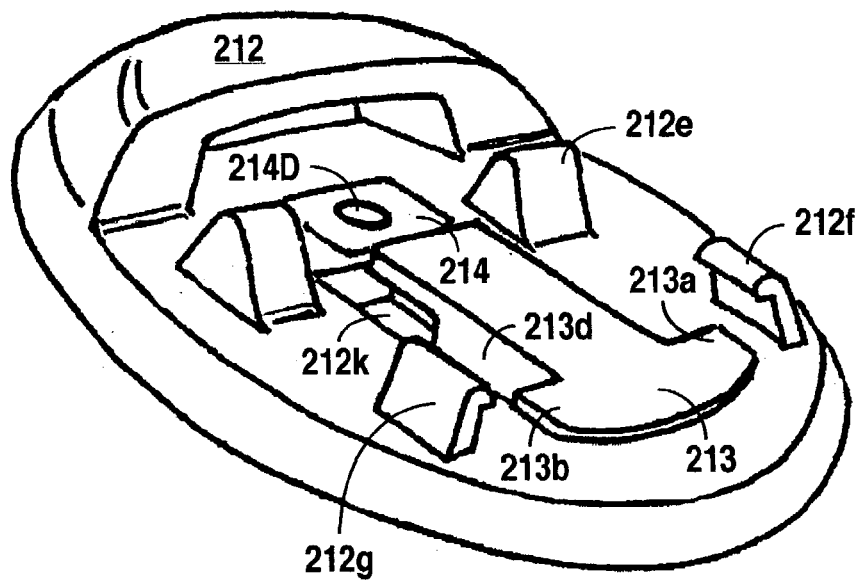
FIG. 24 illustrates yet another embodiment of the present invention base assembly with an open slide.
Figure 25:
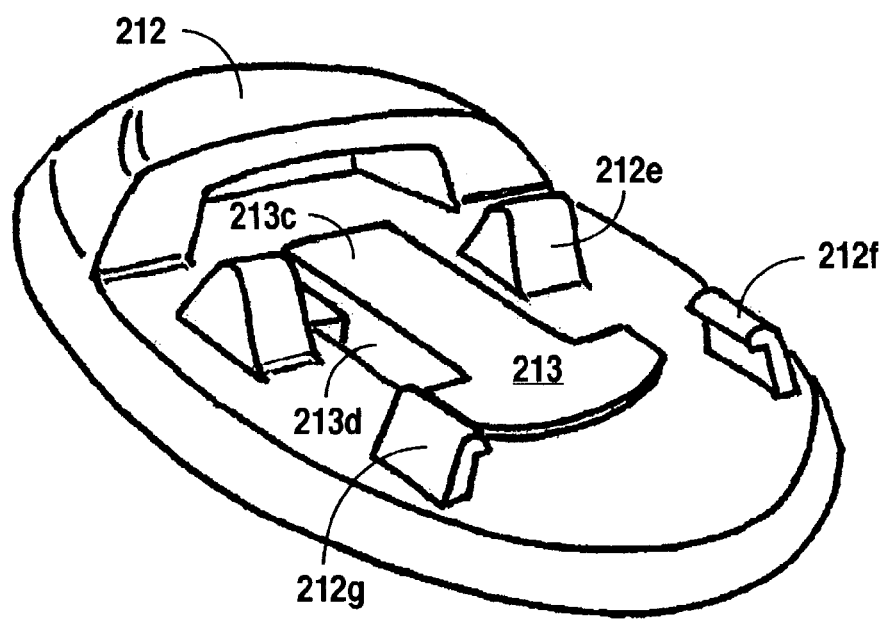
FIG. 25 shows the embodiment of FIG. 24 with the slide closed.
Figure 26:
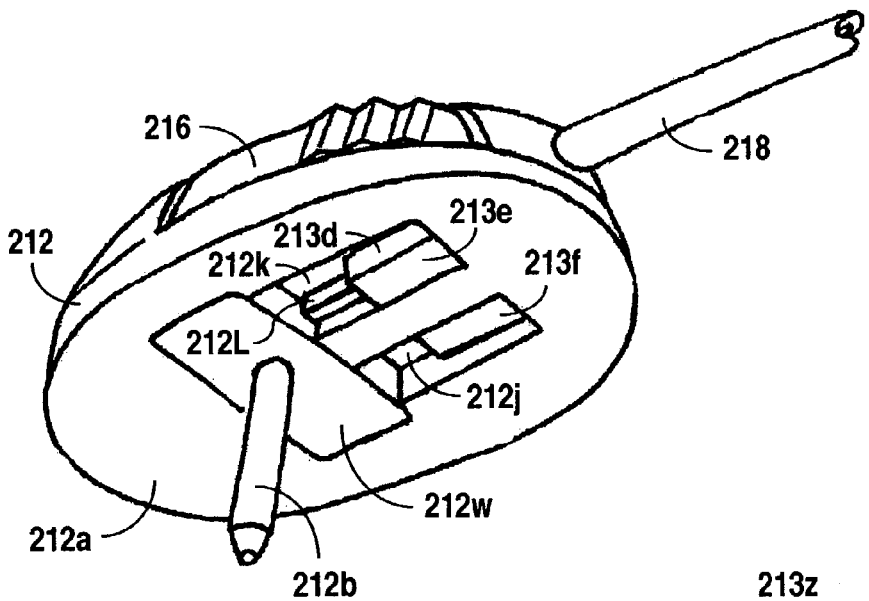
FIG. 26 is a bottom perspective view of an infusion assembly of the present invention showing the open slide position.

Turning now to FIGS. 21 through 29 (alternate embodiments of slide protector), it may be seen that the base may include a protective member or slide 213. The slide is capable of moving from an out of engagement (non-occluding) position to an engagement (occluding) position, the occluding position protecting the fluid channel 214D from collecting debris or releasing liquid when the fluid connector is disengaged from the base. It is seen that slide 213 may include a pair of oppositely mounted ears 213A and 213B, which ears may protrude from a tabular body 213C. The body may include a vertically downwardly depending guide boss 213D with the guide boss having extending from the bottom thereof a pair of guide legs 213E and 231F. Slide 213 is designed for slidable engagement with the base 212 as seen in FIGS. 21–23 and 27–28. More specifically, it is seen that the base may include cam slots 212J and 212K which cam slots may be adjacent to slider channel 212L. Slider channel 212L may be dimensioned for receipt of guide boss 213D therein such that horizontally projecting guide legs 213E and 213F capture the base between the ears of the slide and the guide legs of the slide so that the slide may move between an open or out of engagement position as seen in FIG. 21 to a use or protected position as seen in FIG. 23K, which position protects the base from receiving liquid or debris that may enter the fluid channel therein.

Figure 30:
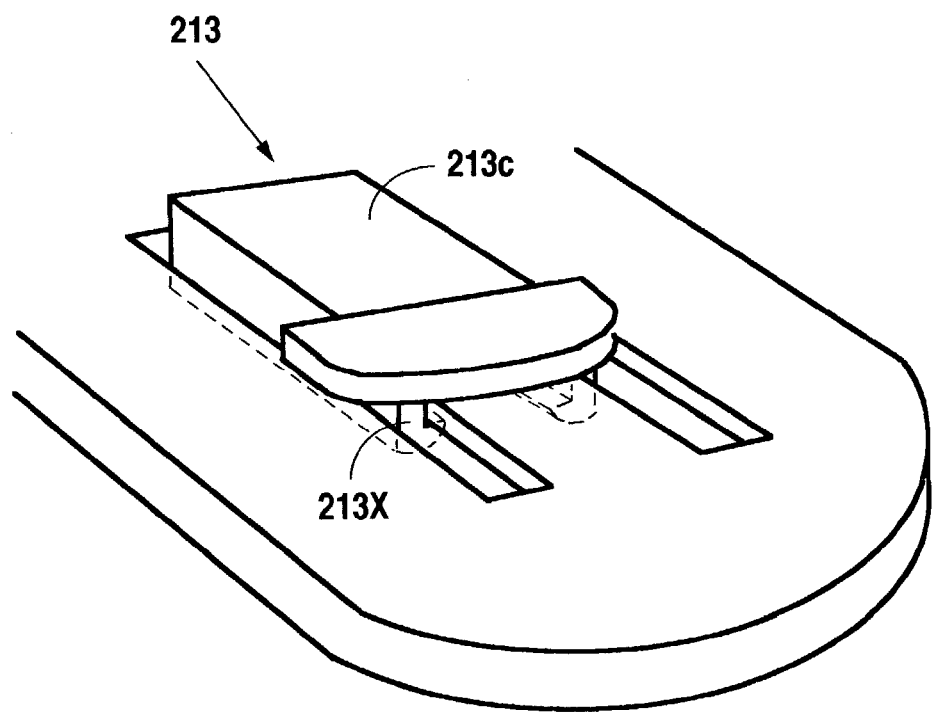
FIG. 30 is a detailed illustration of a slide mechanism of the present invention.
Figure 31:
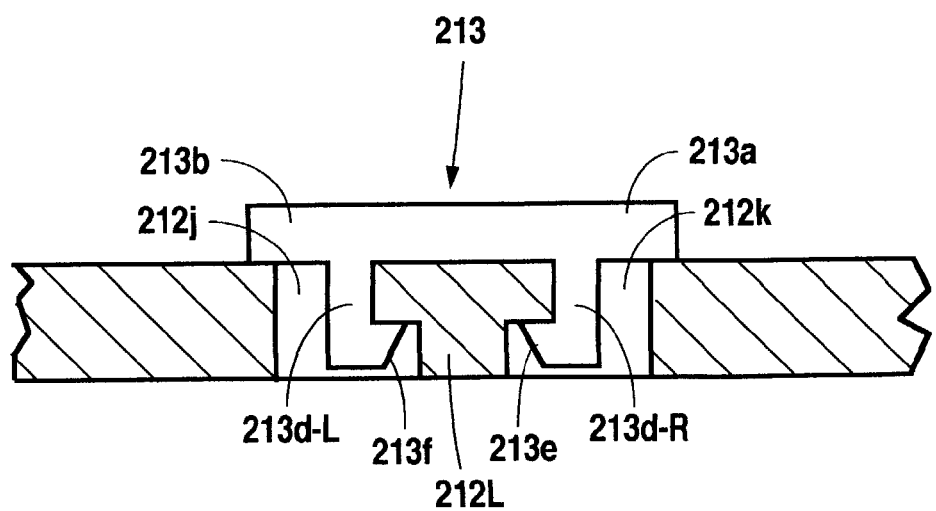
FIG. 31 is a partial cross sectional view of the slide of FIG. 30.

FIGS. 30 and 31 illustrate a preferred embodiment of slide or protective member 213. This embodiment includes only a pair of longitudinal extending guide ridges for resilient engagement to the slots of the base so as to be slideable with the base.

A mechanism for moving the slide between the two positions is provided. When the fluid connector is removed from the base, the slide should be in the protected position placed there manually by the user. When the fluid connector is engaged to the base and urged to the down position, it is seen that the use of a pair of novel cams 216J and 216K (FIG. 23) for engagement with ears 213A and 213B of the slide and slots 212J and 212K as the fluid connector moves towards the down position to urge the slide towards the open position.

Figure 27:
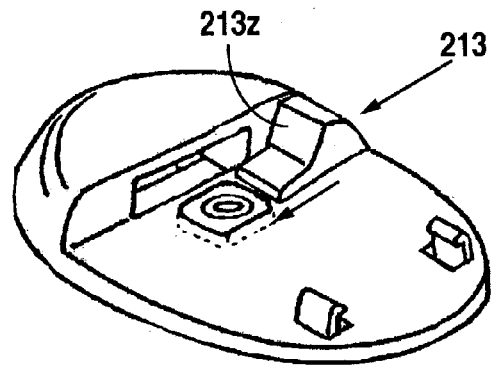
FIG. 27 is a top perspective view of an alternative slide mechanism of the present invention in the open position.
Figure 28:
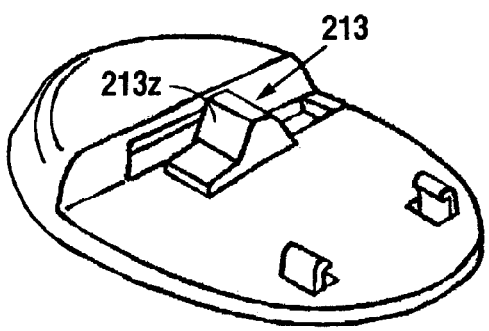
FIG. 28 illustrates the mechanism of FIG. 27 in the protected or closed position.
Figure 29:
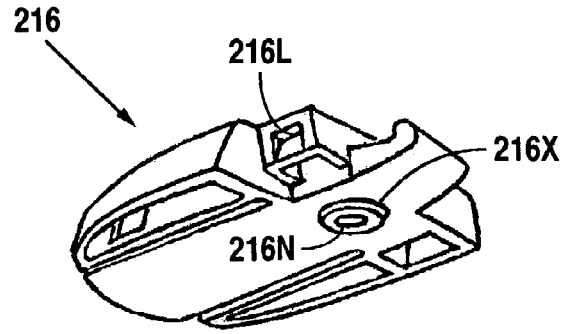
FIG. 29 is a bottom perspective view of a fluid connector for use with the base of FIG. 27 showing the slide positioning mechanism.

FIGS. 27 through 29 illustrate another embodiment of a slide 213 which is also capable of moving between an open (non-occluding) and a protected (occluded) position and wherein the infusion device includes structure to move the slide from the occluded position to the non-occluded position when the fluid connector is moved into the down or delivery position. In this alternate embodiment of the infusion assembly 200, it is seen that a cam surface 216L on the fluid connector will interfere with the shaped top surface 213Z of the slide illustrated in FIG. 28 so that the cam surface urges the slide from a protected position to the open position when the pivoting fluid connector is urged to the down position.

Figure 19:
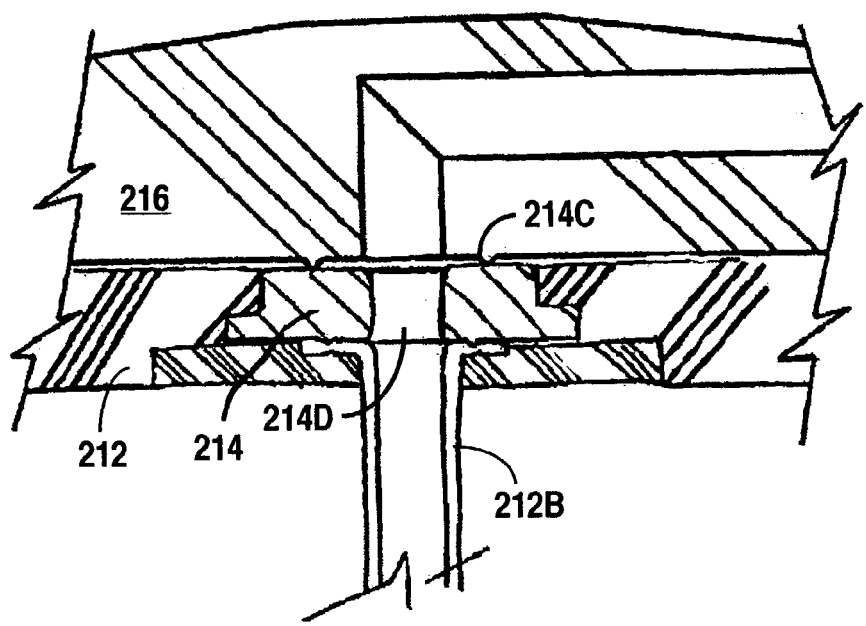
FIG. 19 is a partial cross sectional view of an alternative septumless infusion assembly.
Figure 20:
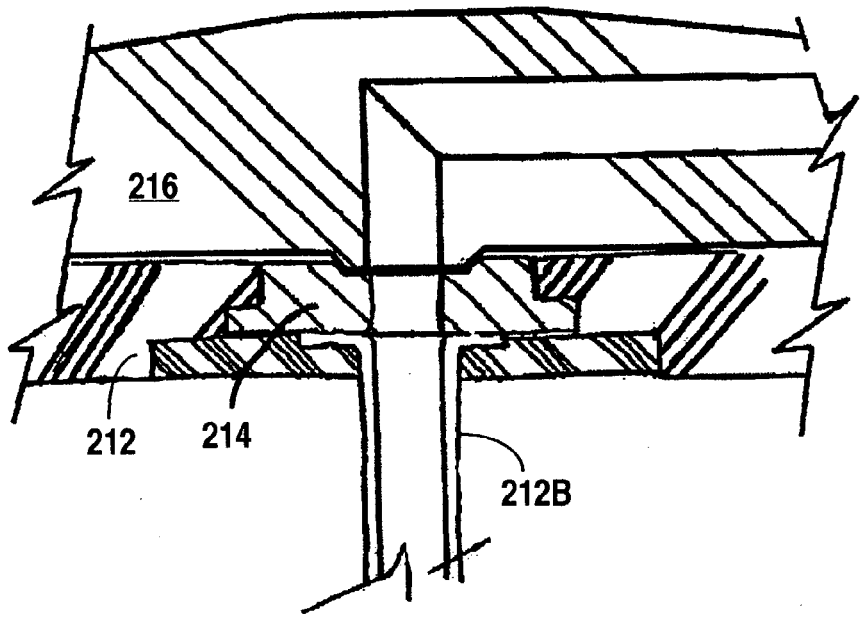
FIG. 20 is a partial cross sectional view of yet another sealing arrangement of the present invention.

Turning now back to the "septumless" sealing means, it may be seen that the pair of members, at least one of which is resilient, may take on a variety of configurations. For example, it has been discussed above that a simple "O" ring in conjunction with interference with a bottom surface of the fluid connector may comprise a fluid sealing pair so as to encircle the joint between the channel of the fluid connector and the channel of the seal or base, so as to join fluid flowing through the fluid connector to the lumen of the cannula and then into the patient. FIG. 19 illustrates a bead 214C on a hard plastic bottom surface of a fluid connector receiving flush against an elastomeric seal adjacent a channel in the seal to join the channel of the fluid connector to the cannula in fluid sealing in relation. FIG. 20 illustrates a circular depression in a resilient sealing member for joining a similarly dimensioned cylindrical projection having canted walls on the bottom surface of the fluid connector when the fluid connector is snapped down into the use position. Again, the figures illustrate paired members, at least one of which is resilient, to encircle the junction of a port in the base to a port in the fluid connector. FIG. 29 illustrates an embodiment of the invention wherein the bottom surface of the fluid connector includes a resilient or non-resilient ridge 216X that includes port 216N. The base may be configured to be flat and either compressible or non-compressible (only if the ridge is compressible) where it meets ridge 216X when the fluid connector moves to the down or use position.

Figure 32:
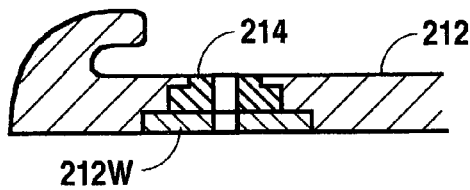
FIG. 32 shows a side elevation, partial cross sectional view of an alternative sealing system of the present invention.
Figure 33:
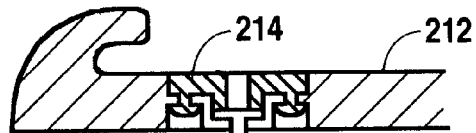
FIG. 33 illustrates yet another sealing system in a partial cross sectional side elevation view.
Figure 33A:
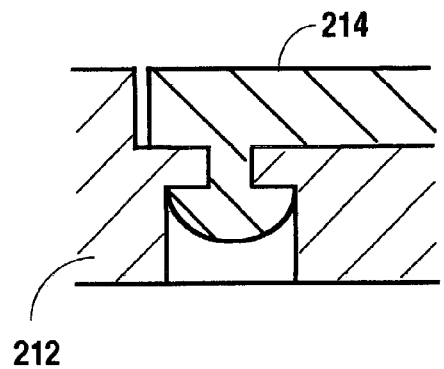
FIG. 33A is a detailed illustration of the engaging tip of the sealing system of FIG. 33.
Figure 34:
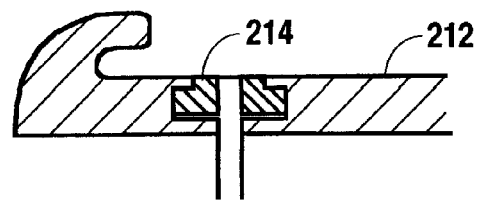
FIG. 34 shows a further alternative sealing system embodiment in a partial cross sectional side elevation view.
Figure 35:
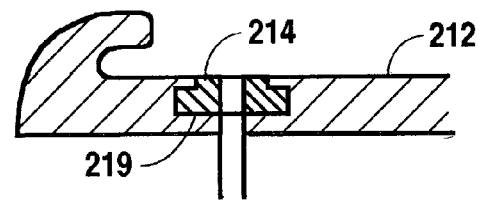
FIG. 35 shows the use of an adhesive for retaining a seal of the present invention.

FIGS. 32 through 35 illustrate a variety of ways in which the seal 214 may be incorporated into base 212. FIG. 32 illustrates walls of the base dimensioned with a lip for receipt of a notch bearing seal thereinto, followed by the receipt of a retaining plate 212W for capturing and integrating the seal into the base. FIGS. 33 and 33A illustrate a seal having resilient legs, the legs having a resilient head thereon, for receipt into bores in the base. FIG. 34 illustrates a base with a cutout dimensioned for receipt of a pliable or resilient projection of the seal thereinto. FIG. 35 illustrates a seal having an adhesive 219 applied thereto to join the seal permanently to the base to "capture" or sandwich a lip on the cannula to the base. Indeed, FIGS. 33 and 34 illustrate that the seal may be used to engage an annular lip on the near end of the cannula to locate and integrate the cannula into the base.

Figure 36:
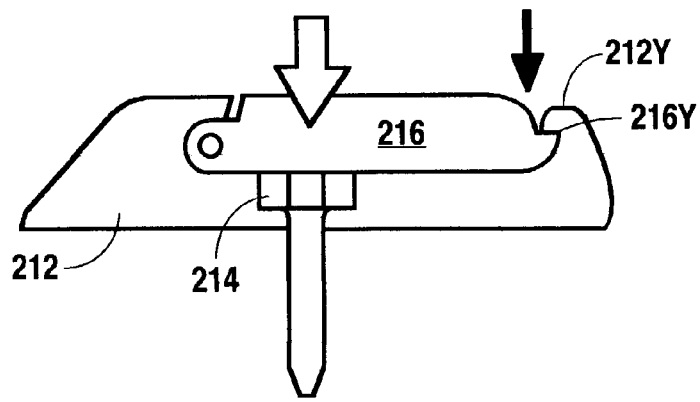
FIG. 36 illustrates the application of varying forces for the connection of the fluid connector to the base assembly of the present invention.

FIG. 36 illustrates yet another novel embodiment of the invention wherein the base 212 may include a lip 212Y bearing extension for engaging a lip 216Y defining a removed end of the fluid connector 216. Further, FIG. 36 illustrates an advantage of the pivoting, "septumless" infusion assembly. Namely, it provides a fluid connector and base wherein one end of the fluid connector is engaged to the base and the other end is dimensioned for receipt of a small force, rotating the fluid connector to a down position, and wherein the fluid connector is designed to releasably and compressibly engage the seal between the pivot end and the rotated end. Thus, a mechanical advantage is applied wherein the resistant force, which must be overcome to create the compression required for an effective seal is between the pivot arm and the small applied force. Indeed, the sealing member in the preferred embodiment can be seen to be closer to the articulation point between the base and the fluid connector in a preferred embodiment illustrated in FIG. 36 closer that is when compared to the distance to the removed end of the fluid connector, where the rotational force is typically applied in moving the fluid connector between an up or non-use position to a down or used position.

Although the invention has been described with reference to a specific embodiments, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. An infusion system for delivery of a fluid from a remote source into a patient's body comprising:
    a main fluid infusion unit having a cannula, said cannula attached at a near end to an underside of said main fluid infusion unit, a first fluid channel in fluid communication with said cannula, and a first hinge section;
    a fluid connection line having a near end and a removed end, said fluid connection line engagable at said removed end to said remote source;
    a fluid connector assembly having a second fluid channel attachable to said near end of said fluid connection line, and a second hinge section;
        said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;
    a first sealing surface surrounding a port opening in said first fluid channel of said main fluid infusion unit; and
    a second sealing surface surrounding a second port opening in said second fluid channel of said fluid connector assembly.

2. The system of claim 1 further comprising:
a main fluid infusion unit emplacement member having an insertion needle, said insertion needle adapted to extend through said main fluid infusion unit and extend beyond a distal end of said cannula when said system is in a first emplacement position.

3. The system of claim 1 further comprising a septum.

4. The system of claim 1 wherein said septum is a one shot fabrication.

5. The system of claim 1 further comprising a septum wherein at least a portion of said septum is positioned above said first fluid channel in said main fluid infusion unit.

6. The system of claim 1 wherein said first sealing surface further comprises a compressible seal member, said compressible seal member cooperating with said second sealing surface to form a seal-to-surface fluid seal connection when said system is in said second delivery position.

7. The system of claim 1 wherein said second sealing surface further comprises a compressible seal member, said compressible seal member cooperating with said first sealing surface to form a seal-to-surface fluid seal connection when said system is in said second delivery position.

8. The system of claim 1 further comprising:
a first fluid channel protector affixed to said main fluid infusion unit for occluding a port opening in said first fluid channel, said protector movable from a first occluding position to a second non-occluding position.

9. The system of claim 8 wherein said fluid connector assembly further comprises:
a protector engagement member, said protector engagement member urging said first fluid channel protector from said first occluding to said second non-occluding position as said fluid connector assembly is pivoted about said first and second hinge sections.

10. The system of claim 8 wherein said main fluid infusion unit further comprises slots cooperating with legs on said first fluid channel protector, said slots adapted to guide said first fluid channel protector from said first occluding position to said second non-occluding position.

11. The system of claim 1 further comprising:
a first fluid channel protector affixed to said main infusion unit for occluding a port opening in said first fluid channel, said first fluid channel protector movable from a first occluding position above said first sealing surface to a second non-occluding position when said system is pivoted from said first non-delivery position to said second delivery position.

12. The system of claim 1 wherein said second hinge section on said first end of said fluid connector assembly is opposite a channel-to-connection line and on said fluid connector assembly, said cooperating first and second hinge sections forming an articulation point such that a closing force applied at said channel-to-connection line and urges said system from said first non-delivery position to said second delivery position.

13. The system of claim 9 wherein said protective member engagement member includes a cam.

14. The system of claim 1 wherein said first hinge section includes walls defining a cutout, and wherein said fluid connector assembly includes a projecting member adapted for pivotal receipt into said cutout.

15. The system of claim 1 wherein said first hinge section includes walls defining a hook and said second hinge section includes an arm for pivotal engagement with said hook.

16. The system of claim 1 wherein said first sealing surface includes an "O" ring.

17. The system of claim 1 wherein said first sealing surface includes a raised bead.

18. The system of claim 1 wherein said second sealing surface includes a raised member.

19. The system of claim 18 wherein said raised member is pliable and dimensioned for compression seating with said first sealing member.

20. The system of claim 1 wherein one of said first or said second sealing surfaces includes raised walls and the other of said first or said second sealing surfaces includes walls defining a depression dimensioned for engagement with said raised walls.

21. The system of claim 1 wherein said fluid connector assembly and said main infusion unit are dimensioned such that, when said fluid connector assembly is in said second delivery position, at least part of said first channel is axially aligned with at least part of said second fluid channel.

22. The system of claim 1 wherein said main fluid infusion unit includes notches and said cannula includes a circular lip at a near end thereof, said notches dimensioned for receipt of said lip therein.

23. The system of claim 22 wherein said first sealing surface engages said lip to locate and retain said cannula integral with said main fluid infusion unit.

24. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source;
a fluid connector assembly having a second fluid channel attachable to said near end of said fluid connection line, and a second hinge section;
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient; and
elements cooperating to releasably lock said fluid connector assembly into said second delivery position.

25. The system of claim 8 further comprising means to releasably lock said fluid connector assembly into said second delivery position.

26. The system of claim 24 wherein said means to releasably lock said fluid connector assembly into said delivery position includes resilient arms on said fluid connector assembly.

27. The system of claim 1 wherein said fluid connector assembly and said main fluid infusion unit are adapted such that said fluid connector assembly is releasable from said main infusion unit when in said non-delivery position.

28. The system of claim 1 wherein said fluid connector assembly and said main fluid infusion unit are adapted to lockably engage one another in said delivery position, said delivery position including when said fluid connector assembly is parallel to the skin of said patient and near end of said fluid connection line engages said fluid connector assembly parallel to said skin of said patient.

29. The system of claim 28 wherein said fluid connector assembly and said main fluid infusion unit are adapted to move from said non-delivery position to said delivery position, said non-delivery position locating said fluid connector assembly approximately vertical with said main infusion unit.

30. The system of claim 24 wherein said fluid connector assembly is adapted to release from said main infusion unit when in said non-delivery position.

31. The infusion system of claim 24 wherein the first fluid channel of the main fluid infusion unit is in axial alignment with the cannula of the main fusion unit and there is no septum in the first fluid channel.

32. The infusion system of claim 24 wherein the fluid connector assembly has no septum as part thereof.

33. The infusion system of claim 24, wherein the first fluid connector assembly has no septum and no needle as part thereof.

34. The infusion system of claim 24, wherein neither the main fluid infusion unit nor the fluid connector assembly has a septum.

35. The infusion system of claim 32, wherein the main fluid infusion unit includes a protective member capable of removably covering an opening in the first fluid channel.

36. The infusion system of claim 35, wherein the main fluid infusion unit includes a protective member capable of removably covering an opening in the first fluid channel of the main infusion unit.

37. The infusion system of claim 35, wherein the protective member is adapted to slide.

38. The system of claim 24 further comprising:
a main fluid infusion unit emplacement member having an insertion needle, said insertion needle adapted to extend through said main fluid infusion unit and extend beyond a distal end of said cannula when said system is in a first emplacement position.

39. The system of claim 24 further comprising a septum.

40. The system of claim 24 wherein said septum is a one shot fabrication.

41. The system of claim 35 further comprising a septum wherein at least a portion of said septum is positioned above said first fluid channel in said main fluid infusion unit.

42. The system of claim 24 further comprising:
a first sealing surface surrounding a port opening in said first fluid channel of said main fluid infusion unit; and
a second sealing surface surrounding a second port opening in said second fluid channel of said fluid connector assembly.

43. The system of claim 42, wherein either of said first or said second sealing surface further comprises a compressible seal member, said compressible seal member cooperating with the other of said first or said second sealing surface to form a seal-to-surface fluid seal connection when said system is in said second delivery position.

44. The system of claim 24 further comprising:
a first fluid channel protector affixed to said main fluid infusion unit for occluding a port opening in said first fluid channel, said protector movable from a first occluding position to a second non-occluding position.

45. The system of claim 44 wherein said fluid connector assembly further comprises:
a protector engagement member, said protector engagement member urging said first fluid channel protector from said first occluding to said second non-occluding position as said fluid connector assembly is pivoted about said first and second hinge sections.

46. The system of claim 44 wherein said main fluid infusion unit further comprises:

slots cooperating with legs on said first fluid channel protector, said slots adapted to guide said first fluid channel protector from said first occluding position to said second non-occluding position.

47. The system of claim 24 further comprising:
a first fluid channel protector affixed to said main infusion unit for occluding a port opening in said first fluid channel, said first fluid channel protector movable from a first occluding position above said first sealing surface to a second non-occluding position when said system is pivoted from said first non-delivery position to said second delivery position.

48. The system of claim 24, wherein said second hinge section on said first end of said fluid connector assembly is opposite a channel-to-connection line and on said fluid connector assembly, said cooperating first and second hinge sections forming an articulation point such that a closing force applied at said channel-to-connection line and urges said system from said first non-delivery position to said second delivery position.

49. The system of claim 45, wherein said protective member engagement member includes a cam.

50. The system of claim 24, wherein said first hinge section includes walls defining a cutout, and wherein said fluid connector assembly includes a projecting member adapted for pivotal receipt into said cutout.

51. The system of claim 24, wherein said first hinge section includes walls defining a hook and said second hinge section includes an arm for pivotal engagement with said hook.

52. The system of claim 42 wherein said first sealing surface includes an "O" ring.

53. The system of claim 42 wherein said first sealing surface includes a raised head.

54. The system of claim 42 wherein said second sealing surface includes a raised member.

55. The system of claim 54 wherein said raised member is pliable and dimensioned for compression seating with said first sealing member.

56. The system of claim 42 wherein one of said first or said second sealing surfaces includes raised walls and the other of said first or said second sealing surfaces includes walls defining a depression dimensioned for engagement with said raised walls.

57. The system of claim 24 wherein said fluid connector assembly and said main infusion unit are dimensioned such that, when said fluid connector assembly is in said second delivery position, at least part of said first channel is axially aligned with at least part of said second fluid channel.

58. The system of claim 24 wherein said main fluid infusion unit includes notches and said cannula includes a circular lip at a near end thereof, said notches dimensioned for receipt of said lip therein.

59. The system of claim 58 wherein said first sealing surface engages said lip to locate and retain said cannula integral with said main infusion unit.

60. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source;

a fluid connector assembly having a second fluid channel attachable to said near end of said fluid connection line, and a second hinge section;

said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient; and a first fluid channel protector affixed to said main fluid infusion unit for occluding a port opening in said first fluid channel, said protector movable from a first occluding position to a second non-occluding position.

61. The system of claim 60, wherein said fluid connector assembly further comprises:

a protector engagement member, said protector engagement member urging said first fluid channel protector from said first occluding to said second non-occluding position as said fluid connector assembly is pivoted about aid first and second hinge sections.

62. The infusion system of claim 60, wherein said main fluid infusion unit further comprises slots cooperating with legs on said first fluid channel protector, said slots adapted to guide said first fluid channel protector from said first occluding position to said second non-occluding position;

a main fluid infusion unit having a cannula, said cannula attached at a near end to an underside of said main fluid infusion unit, a first fluid channel in fluid communication with said cannula, and a first hinge section;

a fluid connection line having a near end and a removed end, said fluid connection line engagable at said removed end to said remote source; and a fluid connector assembly having a second fluid channel attachable to said near end of said fluid connection line, and a second hinge section;

said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient; and said main fluid infusion unit further comprises slots cooperating with legs on said first fluid channel protector, said slots adapted to guide said first fluid channel protector from said first occluding position to said second non-occluding position.

63. An infusion system for delivery of a fluid from a remote source into a patient's body comprising:

a main fluid infusion unit having a cannula, said cannula attached at a near end to an underside of said main fluid infusion unit, a first fluid channel in fluid communication with said cannula, and a first hinge section;

a fluid connection line having a near end and a removed end, said fluid connection line engagable at said removed end to said remote source; and a fluid connector assembly having a second fluid channel attachable to said near end of said fluid connection line, and a second hinge section;

said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;

wherein said second hinge section on said first end of said fluid connector assembly is opposite a channel-to-connection line and on said fluid connector assembly, said cooperating first and second hinge sections forming an articulation point such that a closing force applied at said channel-to-connection line and urges said system from said first non-delivery position to said second delivery position.

64. An infusion system for delivery of a fluid from a remote source into a patient's body comprising:

a main fluid infusion unit having a cannula, said cannula attached at a near end to an underside of said main fluid infusion unit, a first fluid channel in fluid communication with said cannula, and a first hinge section;

a fluid connection line having a near end and a removed end, said fluid connection line engagable at said removed end to said remote source; and a fluid connector assembly having a second fluid channel attachable to said near end of said fluid connection line, and a second hinge section; and said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;

wherein said first hinge section includes walls defining a cutout, and wherein said fluid connector assembly includes a projecting member adapted or pivotal receipt into said cutout.

65. An infusion system for delivery of a fluid from a remote source into a patient's body comprising:

a main fluid infusion unit having a cannula, said cannula attached at a near end to an underside of said main fluid infusion unit, a first fluid channel in fluid communication with said cannula, and a first hinge section;

a fluid connection line having a near end and a removed end, said fluid connection line engagable at said removed end to said remote source; and a fluid connector assembly having a second fluid channel attachable to said near end of said fluid connection line, and a second hinge section;

said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient; and said first hinge section includes walls defining a hook and said second hinge section includes an arm for pivotal engagement with said hook.

66. An infusion system for delivery of a fluid from a remote source into a patient's body comprising:

a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source; and
a fluid connector assembly having a second fluid channel attachable to said near end of said fluid connection line, and a second hinge section; and
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;
wherein said fluid connector assembly and said main fluid infusion unit are adapted such that said fluid connector assembly is releasable from said main infusion unit when in said non-delivery position.

67. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source; and
a fluid connector assembly having a second fluid channel attachable to said near end of said fluid connection line, and a second hinge section;
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;
wherein said first fluid channel of the main fluid infusion unit is in axial alignment with the cannula of the main fusion unit and there is no septum in the first fluid channel.

68. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source; and
a fluid connector assembly having a second fluid channel attachable to said near end of said fluid connection line, and a second hinge section;
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient; and
wherein the fluid connector assembly has no septum as part thereof.

69. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source; and
a fluid connector assembly having a second fluid channel attachable to said near end of said fluid connection line, and a second hinge section;
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;
wherein the first fluid connector assembly has no septum and no needle as part thereof.

70. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source; and
a fluid connector assembly having a second fluid channel attachable to said near end of said fluid connection line, and a second hinge section;
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;
wherein neither the main fluid infusion unit nor the fluid connector assembly has a septum.

71. An infusion system for delivery of a fluid from a remote source into a patient's body comprising:
a main fluid infusion unit having a cannula, said cannula attached at a near end to an underside of said main fluid infusion unit, a first fluid channel in fluid communication with said cannula, and a first hinge section;
a fluid connection line having a near end and a removed end, said fluid connection line engagable at said removed end to said remote source; and
a fluid connector assembly having a second fluid channel attachable to said near end of said fluid connection line, and a second hinge section;
said first hinge section cooperating with said second hinge section to allow pivotal movement of said system from a first non-delivery position wherein said first fluid channel is not in fluid communication with said second fluid channel to a second delivery position wherein said first fluid channel is in fluid communication with said second fluid channel to deliver said fluid from said remote source through said cannula and into said patient;

wherein the said fluid connector assembly and said main fluid infusion unit are releasable when in the non-deliverable position; and wherein said fluid connector assembly and said main infusion unit are adapted to releasably lock together in the delivery position.

* * * * *